US008961987B2

(12) United States Patent
Zolla-Pazner et al.

(10) Patent No.: US 8,961,987 B2
(45) Date of Patent: Feb. 24, 2015

(54) IMMUNOGEN COMPRISING THE HIV GP120 V3 LOOP IN A CONFORMATION THAT INDUCES BROADLY NEUTRALIZING ANTIBODIES

(75) Inventors: Susan Zolla-Pazner, New York, NY (US); Miroslaw K. Gorny, Harrison, NY (US); Timothy J. Cardozo, New York, NY (US); Xiang-peng Kong, New York, NY (US); Ruben Abagyan, La Jolla, CA (US); Maxim Totrov, San Diedo, CA (US); Shan Lu, Franklin, MA (US); Abraham Pinter, Brooklyn, NY (US)

(73) Assignees: New York University, New York, NY (US); Molsoft LLC, La Jolla, CA (US); University of Massachusetts, Boston, MA (US)

( * ) Notice: Subject to any disclaimer, the term of this patent is extended or adjusted under 35 U.S.C. 154(b) by 1021 days.

(21) Appl. No.: 12/195,318

(22) Filed: Aug. 20, 2008

(65) Prior Publication Data

US 2009/0098144 A1    Apr. 16, 2009

Related U.S. Application Data

(60) Provisional application No. 60/956,842, filed on Aug. 20, 2007.

(51) Int. Cl.
| | | |
|---|---|---|
| *A61K 39/21* | (2006.01) | |
| *A61K 39/00* | (2006.01) | |
| *A61K 38/00* | (2006.01) | |
| *C07K 14/005* | (2006.01) | |
| *A61K 38/03* | (2006.01) | |
| *A61K 38/16* | (2006.01) | |

(52) U.S. Cl.
CPC .............. *C07K 14/005* (2013.01); *A61K 38/03* (2013.01); *A61K 38/16* (2013.01); *A61K 39/00* (2013.01); *A61K 39/21* (2013.01); *C07K 2319/35* (2013.01); *C07K 2319/55* (2013.01); *C12N 2740/16122* (2013.01); *C12N 2740/16134* (2013.01)

USPC ................. 424/188.1; 424/192.1; 424/207.1; 514/1.1; 514/3.8

(58) Field of Classification Search
CPC ... A61K 39/07; A61K 39/21; A61K 2300/00; A61K 2039/5256; A61K 2039/53; A61K 2039/64; A61K 2039/5158; A61K 2039/523; A61K 2039/542; A61K 2039/54; A61K 2039/55; A61K 2039/6037; A61K 39/00; A61K 2039/541; A61K 2039/55522; A61K 2039/55538; A61K 2039/55544; A61K 2039/55555; A61K 2039/6087; C07K 14/005; C07K 2319/35; C07K 2319/55; C07K 14/001; C07K 14/245; C07K 14/28; C07K 1/04; C07K 9/001; C12N 2740/16122; C12N 2740/16134; C12N 15/86; C12N 2270/36143; C12N 2770/36162; C12N 2795/12043; C12N 2830/002; C12N 2830/55; C12N 2840/203; C12N 2710/24143; C12N 2740/16034; Y10S 530/826; C12P 21/005

See application file for complete search history.

(56) References Cited

PUBLICATIONS

Backsrom et al., Gene, 1995, 165:163-171.*

* cited by examiner

*Primary Examiner* — Nicole Kinsey White
(74) *Attorney, Agent, or Firm* — Browdy and Neimark, PLLC

(57) ABSTRACT

Insertion of HIV-1 V3 loop peptides from the viral glycoprotein gp120 into selected, immunogenic scaffold proteins results in a recombinant polypeptide that is a potent V3 immunogen. V3 immunogens include natural and consensus V3 sequences and cyclic and reverse peptides. Preferred scaffold proteins are Cholera Toxin subunit B and homologues thereof including closely related *E. coli* enterotoxins. Such immunogenic polypeptides induce broadly reactive anti-gp120 antibodies specific for V3 epitopes that can neutralize heterologous HIV-1 subtypes and strains. These polypeptide, methods for preparing them, and methods for inducing anti-gp120 (V3-specific) antibody) responses using them are disclosed.

35 Claims, 2 Drawing Sheets

IMMUNOGEN COMPRISING THE HIV GP120 V3 LOOP IN A CONFORMATION THAT INDUCES BROADLY NEUTRALIZING ANTIBODIES

BACKGROUND OF THE INVENTION

1. Field of the Invention

The present invention relates, in general, to an immunogen for inducing antibodies that neutralize a wide spectrum of HIV primary isolates and to methods of inducing anti-HIV antibodies using this immunogen.

2. Description of the Background Art

Effective vaccination against HIV remains the only viable means to stop the spread of the AIDS pandemic. However, numerous attempts to elicit protective immunity to HIV have been unsuccessful.

The majority of antibodies generated against the HIV envelope glycoprotein gp120 are not neutralizing, either because their binding does not prevent fusion of HIV to its target cells or because the epitopes they recognize are inaccessible to the antibody. Therefore focusing the immune response to regions of gp120 that are known to bind neutralizing antibodies may improve the efficacy of vaccination. With few exceptions, even antibodies with neutralizing activity are only reactive against a limited number of HIV strains, a result of most antibody epitopes being subject to high sequence variability.

The V3 region of gp120, while generally variable, possesses conserved features that allow broad neutralization by certain antibodies such as the human monoclonal antibody (mAb) 447-52D (also referred to herein as 447-52 and 447). 447-52D recognizes the conserved tip of the V3 loop in a β-turn conformation.

However, most anti-V3 antibodies have narrow neutralization profiles. A specially designed V3-based immunogen that could induce high titers of antibodies with a binding mode and epitope specificity that is similar to that of one or more known broadly neutralizing antibodies (for example, 447-52D) is expected to be valuable as ah HIV vaccine.

Cholera Toxin subunit B ("CTB") and a family of closely related bacterial proteins such as *E. coli* enterotoxins are homopentamers made of relatively small subunits (~100 aa). The protein is highly immunogenic and has been used generally in fusion constructs to enhance immunogenicity of its fusion partner polypeptide or peptide. (McKenzie, S J et al., *J Immunol* 1984, 133:1818-24; Czerkinsky, C et al., *Infec Immun* 1989, 57:1072-7; Lipscombe, M et al., *Mol Microbiol* 1991, 5:1385-92). CTB has been described as a mucosal adjuvant for vaccines. Arêas A P et al., *Biochem Biophys Res Commun.* 2004, 321:192-6, genetically fused the ctxB gene to the psaA gene from *Streptococcus pneumoniae*, a surface protein, a vaccine antigen candidate. Purified CTB-PsaA expressed in *E. coli*, was used for intranasal immunization of mice and induced systemic and mucosal antibodies in serum, saliva, and in nasal and bronchial wash samples.

An important factor for the immunogenic property of CTB and related toxins is their binding to GM1 ganglioside. X-ray structures of CTB revealed that the oligosaccharide binding sites are formed by residues E51, Q56, H57, Q61, W88, N90, and K91 (Sixma T K et al., 1992, *Nature* 355; 561-4). The availability of this structural information allows protein design that avoids or minimizes disruption of the CTB GM1 binding site, thereby preserving the inherent immunogenicity of these polypeptides. Harakuni T et al., *Infect Immun.* 2005, 73:5654-65, disclosed that when used as a delivery means of a vaccine to mucosal immune systems, CTB cannot tolerate large-protein fusion which impairs pentamerization and lowers affinity for GM1-ganglioside. A new strategy to reduce steric hindrance between CTB-antigen fusion subunits promoted integration of unfused CTB "molecular buffers" into the pentamer unit, leading to more efficient self-assembly into biologically active pentamers. The chimeric protein took on a compact configuration, becoming small enough to be secreted. Affinity-purified proteins administered by a mucosal route induced specific immune responses in mice, a finding that was considered broadly applicable to bacterial enterotoxin-based vaccine design.

Its propensity to induce mucosal immunity is another advantage of CTB as an immunogenic "carrier" that is uncommon, yet is highly desirable for an HIV immunogen or vaccine because infection commonly occurs via a mucosal route. Furthermore, CTB is not toxic without the concomitant presence of the A subunit (that is part of the native cholera toxin. CTB has been approved as a component of an anticholera vaccine for use in humans.

In an attempt to generate an immunogen competent to generate 447-52D-like antibodies, Chakraborty et al., (*Biochem. J.* 399:483-91) inserted the known epitope of 447-52D at three different surface loop locations in the small, stable protein *Escherichia coli* thioredoxin (Trx). At one of the three locations (between residues 74 and 75), the insertion was tolerated (i.e., the resulting protein was stable and soluble) and bound 447-52D with an affinity similar to that of intact gp120. Upon immunization, with the V3 peptide-Trx scaffold, anti-V3 antibodies were induced that could compete for 447-52D binding to gp120. These anti-V3 antibodies were said to recognize the same epitope as 447-52D. The 447-52D-lik Abs were estimated to be present at concentrations of 50400 μg/ml of serum and were unable to effect neutralization of HIV-1 strains like JR-FL and BAL but could neutralize the sensitive MN strain. The authors suggested that because of the low accessibility of the V3 loop on primary HIV-1 isolates such as JRFL, it will be difficult to elicit a V3-specific, 447-52D-like antibody response to effectively neutralize such isolates.

It has also been observed that if the HIV-MN V3 epitope is placed in a scaffold, only strain-specific neutralization (of the MN strain) occurs. In contrast, the immunogenic compositions of the present invention surprisingly result in antibody responses that neutralize heterologous HIV-1 virus, as exemplified herein. Immunization with a combination of CTB+V3 as conceived by the present inventors was unexpectedly effective in inducing cross-clade antibody responses (see Examples).

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention provides a recombinant immunogenic polypeptide comprising a V3 loop peptide of the HIV gp120 protein (or a fragment, variant, homologue or derivative thereof as described herein), inserted into an immunogenic scaffold protein, wherein (a) the presence of the V3 loop peptide, fragment, variant, homologue or derivative in the scaffold protein induces a conformation in the V3 peptide that is recognized by and bound by a broadly neutralizing anti-HIV-1 antibody, and (b) when used as an immunogen, the polypeptide induces a broadly-neutralizing antibody response, preferably a mucosal antibody response, which neutralizes heterologous HIV-1 viruses. The scaffold protein is preferably one which binds to an oligosaccharide structure of ganglioside GM1, and the scaffold protein into which into the V3 loop peptide is inserted retains the GM1 binding activity. Another preferred property of the scaffold protein is its propensity to induce mucosal immunity, so that, upon immunization, the recombinant, V3-containing construct of the present invention induces mucosal immunity, including formation of IgA antibodies which are better able to bind HIV-1 virions which enter the body via the mucosa.

The scaffold protein is preferably a cholera toxin subunit B (CTB), preferably SEQ ID NO:1 (GenBank Accession No. AAC34728) or fragment thereof, or a homologue thereof which shares at least 50% amino acid sequence identity with CTB. Higher degrees of sequence identity are preferred, as described below. In another embodiment, the scaffold protein is an *E. coli* enterotoxin, preferably heat-labile enterotoxin having GenBank Accession No. AAC60441 and the sequence SEQ ID NO:2). While this protein has been used as a scaffold for delivery of or vaccination against certain proteins (see Background), the inventors know of no instances when an HIV protein or peptide has been inserted, attached, or fused to CTB. Based on the observations of Chakraborti et al. (supra) using thioredoxin as a scaffold for an HIV antigen, there would be no expectation that an HIV protein or peptide bound to or inserted in a scaffold protein (which thioredoxin represents) would result in anything other than a type-specific antibody response rather than the broadly-neutralizing responses disclosed herein.

The above immunogen is preferably one that is recognized and bound by a broadly neutralizing human anti-gp120 antibody, preferably mAb 447-52D or 2219 or 2557.

A preferred the immunogenic polypeptide in which a consensus V3 peptide of an HIV-1 subtype or clade is inserted into CTB is a polypeptide the sequence of which is SEQ ID NO:3 or SEQ ID NO:5.

In the above immunogenic polypeptide, the V3 loop peptide
(a) is preferably a sequence present in an HIV-1 virus of subtype B, or comprises a subtype B consensus sequence;
(b) is preferably a sequence present in an HIV-1 virus or subtype C, or comprises a subtype C consensus sequence;
(c) is preferably a sequence present in an HIV-1 virus of subtype H, or comprises a subtype H consensus sequence;
(d) preferably comprises a sequence of HIV-1 of strain JRCSF.

In other embodiments, the polypeptide may comprise a V3 sequence of virus of any other clade or subtype of HIV-1 or a consensus V3 sequence of any other subtype or clade.

In another embodiment of the above immunogenic polypeptide, the V3 loop peptide is a cyclic peptide, such as a cyclic peptide that comprises TRKSIRIGRGQTFYA (residues 3-17 of SEQ ID NO:8), or a homologue thereof from a different HIV-1 virus or a homologous V3 consensus sequence from a different HIV-1 subtype.

In another embodiment of the above immunogenic polypeptide, the V3 loop peptide is a reverse peptide which is organized to include, in the order N-terminal to C terminal:
  (i) a beta strand sequence of the V3 C terminal region,
  (ii) a connector peptide, such as Ala-Ser-Ser-Pro (residues 6-9 of SEQ ID NO:10) or Ser-Gly-Pro (residues 19-21 of SEQ ID NO:14).
  (iii) a beta strand sequence of the V3 N terminal region.

Preferred reverse peptides include CQAFYASSPRKSIHI-GAC (SEQ ID NO:10) and CQAFYATGDIIGDIRQAHSG-PNNTRKSIHIGAC (SEQ ID NO:14). The reverse peptides may be inserted into scaffold peptide, a preferred example of which is (SEQ ID NO:15)
TPQNITDLCAEYHNTQIHTLNDKIFSYTESLAGKREMAIITFCQAFYASS

PRKSIHIGACATFQVEVPGSQHIDSQKKAIERMKDTLRIAYLTEAKVEKL

CVWNNKTPRAIAAISMAN.

The present invention also provides an immunogenic pharmaceutical composition comprising an immunogenic polypeptide as described above and elsewhere in this document and an immunologically and pharmaceutically acceptable vehicle or excipient.

This pharmaceutical composition may also comprise an adjuvant or an immunostimulatory peptide or polypeptide different from said immunogenic polypeptide. The immunostimulatory polypeptide is preferably a cytokine. In a preferred embodiment, the adjuvant and/or the immunostimulatory peptide or polypeptide is one that promotes generation of mucosal immunity.

In a preferred embodiment, the adjuvant is selected from the group consisting of:
  (a) ISAF-1 (5% squalene, 2.5% pluronic L121, 0.2% Tween 80) in phosphate-buffered solution with 0.4 mg of threonyl-muramyl dipeptide;
  (b) de-oiled lecithin dissolved in an oil (e.g., AMPHI-GEN™);
  (c) aluminum hydroxide gel;
  (d) a mixture of (b) and (c)
  (e) QS-21;
  (f) monophosphoryl lipid A adjuvant; and
  (g) incomplete Freund's adjuvant.

The present invention is also directed to a method for inducing a broadly neutralizing antibody response against a V3 epitope of HIV-1 gp120 in a subject in need thereof, comprising administering to the subject an effective amount of the immunogenic polypeptide described herein, or an immunogenic pharmaceutical composition as described herein wherein the response results in antibodies that neutralize HIV-1 viruses heterologous to the virus strain or subtype from which the immunogenic polypeptide was derived. The method preferably induces an antibody response in which broadly reactive antibodies, preferably neutralizing antibodies, more preferably a mucosal antibody response. The present invention also includes a kit comprising in separate compartments in close proximity therein:
  (a) one or more unit dosages of the above immunogenic polypeptide or said pharmaceutical composition as above, and
  (b) instructions for administering the immunogenic composition to a subject for inducing the broadly neutralizing antibody response.

The kit may further comprise an adjuvant or immunostimulatory protein different from the fusion protein, and instructions for administering the adjuvant or immunostimulatory protein.

DESCRIPTION OF THE PREFERRED EMBODIMENTS

Figure 1:
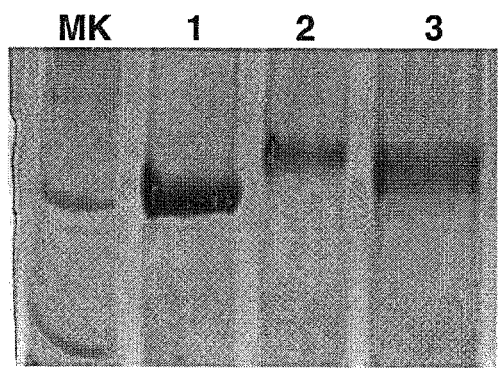
FIG. 1 shows a Western blot that confirms the expression of Immunogens I and II. Lane 1: Wt CTB; Lane 2: Immunogen I (SEQ ID NO:3); Lane 3: Immunogen II (SEQ ID NO:5).

The present invention relates to an immunogen that induces broadly neutralizing antibodies against HIV-1. In a preferred embodiment, the immunogen is a recombinant protein comprising all or most of the scaffold polypeptide Cholera Toxin subunit B (CTB) (GenBank Accession No. AAC34728; See also, World Wide Web URL mbs.cbrc.jp/htbin/bget_pdh?1JR0)

```
                                            (SEQ ID NO:1)
MIKLKFGVFF TVLLSSAYAH GTPQNITDLC AEYHNTQIHT

LNDKIFSYTE SLAGKREMAI ITFKNGATFQ VEVPGSQHID

SQKKAIERMK DTLRIAYLTE AKVEKLCVWN NKTPHAIAAI

SMAN 124
```

The recombinant protein immunogen also comprises a V3 loop fragment of the gp120 HIV envelope protein inserted into scaffold sequence.

Other useful scaffolds for the construct of the present invention include a family of closely related bacterial proteins which are homopentamers of relatively small subunits (~100 aa). It is preferred that the scaffold protein be one that, like CTB, is highly immunogenic and capable of enhancing the immunogenicity of any heterologous sequences fused to/inserted n it (whether internally or at either terminus).

A preferred scaffold protein is one that is immunogenic. One preferred embodiment is a scaffold protein that, like CTB, includes a binding site for the oligosaccharide portion of ganglioside $GM_1$ in membranes. X-ray analysis of CTB revealed an oligosaccharide binding site formed by residues E51, Q56, H57, Q61, W88, N90, K91 (Sixma T K et al., 1992, *Nature* 355:561-4.) Despite the use of CT as an immunogenic scaffold (see Background section), it was nevertheless unexpected to find that various HIV-1 V3 loop peptides and molecules derived therefrom, such as cyclic peptides and reverse peptides (discussed below) showed potent binding by anti HIV-1 mAbs, and induced more broadly-neutralizing Ab responses against V3's of various viral subtypes or clades.

Other polypeptides that share the advantageous properties of CTB are also intended within the scope of this invention as scaffolds for various V3 molecules to produce broadly neutralizing Ab response in vivo. One example of an *E. coli* enterotoxin useful as a scaffold protein herein is heat-labile enterotoxin B subunit, also referred to as LTc B (GenBank Accession No. AAC60441), a 124 residue polypeptide (SEQ ID NO:2) which sequence is shown below.

```
MNKVKCYVLF TALLSSLCAY GAPQSITELC SEYRNTQIYT

INDKILSYTE SMAGKREMVI ITFKSGATFQ VEVPGSQHID

SQKKAIERMK DTLRITYLTE TKIDKLCVWN NKTPNSIAAI

SMEN 124
```

The following terms are used in the disclosure of sequences and sequence relationships between two or more nucleic acids or polypeptides: (a) "reference sequence", (b) "comparison window", (c) "sequence identity", (d) "percentage of sequence identity", and (e) "substantial identity".

As used herein, "reference sequence" is a defined sequence used as a basis for sequence comparison. A reference sequence may be a subset or the entirety of a specified sequence; for example, as a segment of a full-length cDNA or other polynucleotide sequence, or the complete cDNA or polynucleotide sequence. The same is the case for polypeptides and their amino acid sequences.

As used herein, "comparison window" includes reference to a contiguous and specified segment of a polynucleotide or amino acid sequence, wherein the sequence may be compared to a reference sequence and wherein the portion of the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of nucleotide and amino acid sequences for comparison are well-known in the art. For comparison, optimal alignment of sequences may be done using any suitable algorithm, of which the following are examples:

(a) the local homology algorithm ("Best Fit") of Smith and Waterman, *Adv. Appl. Math.* 2: 482 (1981);
(b) the homology alignment algorithm (GAP) of Needleman and Wunsch, *J. Mol. Biol.* 48: 443 (1970); or
(c) a search for similarity method (FASTA and TFASTA) of Pearson and Lipman, *Proc. Natl. Acad. Sci.* 85 2444 (1988);

In a preferred method of alignment, Cys residues are aligned. Computerized implementations of these algorithms, include, but are not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG) (Madison, Wis.). The CLUSTAL program is described by Higgins et al., *Gene* 73:237-244 (1988); Higgins et al., *CABIOS* 5:151-153 (1989); Corpet et al., *Nucl Acids Res* 16:881-90 (1988); Huang et al., *CABIOS* 8:155-65 (1992), and Pearson et al., *Methods in Molecular Biology* 24:307-331 (1994).

A preferred program for optimal global alignment of multiple sequences is PileUp (Feng and Doolittle, *J Mol Evol* 25:351-360 (1987) which is similar to the method described by Higgins et al. 1989, supra).

The BLAST family of programs which can be used for database similarity searches includes: BLASTN for nucleotide query sequences against database nucleotide sequences; BLASTX for nucleotide query sequences against database protein sequences; BLASTP for protein query sequences against database protein sequences; TBLASTN for protein query sequences against database nucleotide sequences; and TBLASTX for nucleotide query sequences against database nucleotide sequences. See, for example, Ausubel et al., eds., *Current Protocols in Molecular Biology*, Chapter 19, Greene Publishing and Wiley-Interscience, New York (1995) or most recent edition. Unless otherwise stated, stated sequence identity/similarity values provided herein, typically in percentages, are derived using the BLAST 2.0 suite of programs (or updates thereof) using default parameters. Altschul et al., *Nucl Acids Res.* 25:3389-3402 (1997).

As is known in the art, BLAST searches assume that proteins can be modeled as random sequences. However, many real proteins comprise regions of nonrandom sequence which may include homopolymeric tracts, short-period repeats, or regions rich in particular amino acids. Alignment of such regions of "low-complexity" regions between unrelated proteins may be performed even though other regions are entirely dissimilar. A number of low-complexity filter programs are known that reduce such low-complexity alignments. For example, the SEG (Wooten et al., 1993, *Comput. Chem.* 17:149-63) and XNU (Claverie et al., 1993, *Comput. Chem.,* 17:191-201) low-complexity filters can be employed alone or in combination.

As used herein, "sequence identity" or "identity" in the context of two nucleic acid or amino acid sequences refers to the nucleotides or amino acid residues in the two sequences which are the same when the full sequence is aligned for maximum correspondence over a specified comparison window. It is recognized that when using percentages of sequence identity for proteins, a residue position which is not identical often differs by a conservative amino acid substitution, where a substituting residue has similar chemical properties (e.g., charge, hydrophobicity, etc.) and therefore does not change the functional properties of the polypeptide. Where sequences differ in conservative substitutions, the % sequence identity may be adjusted upwards to correct for the conservative nature of the substitution, and be expressed as "sequence similarity" or "similarity" (combination of identity and differences that are conservative substitutions). Means for making this adjustment are well-known in the art. Typically this involves scoring a conservative substitution as a partial rather than as a full mismatch, thereby increasing the percentage sequence identity. Thus, for example, where an identical amino acid is given a score of "1" and a non-conservative substitution is given a score of "0" zero, a conservative substitution is given a score between 0 and 1. The scoring of conservative substitutions is calculated, e.g., according to the algorithm of Meyers et al., *CABIOS* 4:11-17 (1988) as implemented in the program PC/GENE (Intelligenetics, Mountain View, Calif., USA).

As used herein, "percentage of sequence identity" refers to a value determined by comparing two optimally aligned sequences over a comparison window, wherein the portion of the nucleotide or amino acid sequence in the comparison window may comprise additions or deletions (i.e., gaps) as compared to the reference sequence (which lacks such additions or deletions) for optimal alignment, such as by the GAP algorithm (supra). The percentage is calculated by determining the number of positions at which the identical nucleotide or amino acid residue occurs in both sequences to yield the number of matched positions, dividing that number by the total number of positions in the window of comparison and multiplying the result by 100, thereby calculating the percentage of sequence identity.

The term "substantial identity" of two sequences means that a polynucleotide or polypeptide comprises a sequence that has at least 60%, preferably at least 70%, more preferably at least 80%, even more preferably at least 90%, and most preferably at least 95% sequence identity to a reference sequence using one of the alignment programs described herein using standard parameters. Values can be appropriately adjusted to determine corresponding identity of the proteins encoded by two nucleotide sequences by taking into account codon degeneracy, amino acid similarity, reading frame positioning, etc.

One indication that two nucleotide sequences are substantially identical is if they hybridize to one other under stringent conditions. Because of the degeneracy of the genetic code, a number of different nucleotide codons may encode the same amino acid. Hence, two given DNA sequences could encode the same polypeptide but not hybridize under stringent conditions. Another indication that two nucleic acid sequences are substantially identical is that the polypeptide encoded by the first nucleic acid is immunologically cross reactive with the polypeptide encoded by the second nucleic acid. Clearly, then, two peptide or polypeptide sequences are substantially identical if one is immunologically reactive with antibodies raised against the other. A first peptide is substantially identical to a second peptide, if they differ only by a conservative substitution. Peptides which are "substantially similar" share sequences as noted above except that nonidentical residue positions may differ by conservative substitutions.

In a preferred embodiment, the length of a sequence being compared is at least 30%, preferably at least 40%, more preferably at least 50%, even more preferably at least 60%, and even more preferably at least 70%, 80%, or 90% of the length of the reference sequence, for example, wild-type CTB.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers et al., supra or into the ALIGN program (version 2.0), using a PAM120 weight residue table, a gap length penalty of 12 and a gap penalty of 4.

The scaffold polypeptide or protein of the present invention preferably has at least about 50% sequence identity with CTB (or with LTc B). More preferably, the sequence identity with CTB is 55%, 60%, 65%, 70%, 75%, 80%, 85%, 90%, 91%, 92%, 93%, 94%, 95%, 96%, 97%, 98%, or 99% (or any intermediate value between the percent identity shown above).

Direct insertion, as opposed to the more commonly used fusion via a linker, allows the immunogenic scaffold to impose constraints on the termini of the V3 loop. Appropriate choice of the insert length and position are exploited to induce in the loop the desired conformation in which conserved epitopes are exposed. Exposure of these conserved epitopes confers on the immunogen the ability to induce a broadly neutralizing Ab response.

Available structural information on V3 peptides complexed with neutralizing antibodies suggests two different binding modes and epitopes associated with broad neutralization:

(1) Complex with Ab447-52D (Stanfield, R L et al., *Structure* 2004, 12:193-204).

The epitope consists primarily of the backbone atoms of V3 loop (2) Complex with Ab2219 (Stanfield, R L et al., *J Virol* 2006, 80:6093-6105).

Antibody contacts mostly side-chain atoms of V3, but the amino acids involved are highly conserved in the V3 sequence—four side-chains that form a hydrophobic cluster and two positively charged side-chains.

Molecular modeling is used to test in-silico, whether various insertion positions in the scaffold and different loop lengths result in loop conformations that present one of these two conserved epitopes. Specifically, the present inventors have employed two approaches:

(A) The scaffold is scanned for amino-acid positions that can be superimposed on the termini of the loop as observed in the V3/antibody complex. When superposition within small tolerances (<0.5 Å root mean square deviation (RMSD) for the terminal residues is achieved, the model is evaluated for the absence of clashes with the scaffold structure.

(B) The loop is inserted in a random conformation and subjected to conformational sampling. Low energy conformations generated during sampling are compared to the desired V3 conformation as observed in the V3/antibody complex. Sampling is over a restricted energy range. When the construct is such that conformations within 1.0 Å backbone RMSD of the desired V3 conformation are identified in the simulation, a model of the immunogen-antibody complex is built to ensure that the scaffold does not interfere with the V3 loop/antibody binding.

The foregoing descriptions of sequence similarity, homology, etc., with respect to the scaffold protein are also applicable to the HIV-1 antigenic sequences, with an emphasis on V3 loop peptide sequences. Various approaches are described herein to generate novel V3 peptide sequences, which include variants and functional derivatives (e.g., cyclic peptides, reverse peptides, etc., that maintain the correct structural characteristic so that the peptide or derivative is antigenic, and, more preferably, immunogenic in a subject in whom a broadly-reactive anti-HIV-1 antibody response is sought). A V3 peptide (which term is defined as including a variant or functional derivative of a natural V3 peptide is then used to create an producing recombinant immunogenic polypeptide by introduction into the sequence and tertiary structure of a scaffolding protein. The descriptions herein utilize particular sequences, such as consensus sequences of particular viral subtypes or clades, or sequences taken from particular HIV-1 strains. It should be understood, however, that the present invention also comprehends homologues, fragments, mutants or variants (such as conservative amino acid substitution variants) as indicated above and as discussed further below in describing cyclic and reverse peptides.

The smaller the scaffold used for the construct, the fewer are the number of potential "irrelevant" epitopes it carries. In a preferred embodiment, the design of a construct uses a relatively small oligomeric scaffold, generally >50 residues and less than about 1000 residues, preferably at least about 100 residues into which is inserted the V3 peptide which term is defined as including a variant or functional derivative of a natural V3 peptide.

The V3 peptide is preferably inserted directly into the scaffold's tertiary structure. This yields a polypeptide in which an exceptionally high fraction of the molecular surface presents relevant epitopes, in this case V3 epitopes that (1) are recognized by broadly-reactive neutralizing anti-gp120 antibodies and (2) can elicit anti-HIV-1 antibody responses that preferably are broadly-reactive and neutralize the virus. A "broadly reactive" or "broadly neutralizing" antibody or antibody response is an antibody or response that results in binding and neutralization of at least one group of heterologous HIV-1 viruses, that are members of a different subtype of clade than that of the source of the immunizing antigen, generally a V3 epitope. Preferably a broadly reactive antibody neutralizes viruses of at least 2 subtypes or clades, or viruses of at least 3 or 4 subtypes or clades. Preferably the antibodies induced by the present immunogenic polypeptides are mucosal antibodies that are capable of neutralizing HIV-1 virions in mucosal sites or spaces. Mucosal immunity is well-known in the art, and is described in standard textbooks of immunology, for example, A. K. Abbas et al., *Cellular and Molecular Immunology* (Fourth Ed.), W.B. Saunders Co., Philadelphia, 2000; C. A. Janeway et al., *Immunobiology. The Immune System in Health and Disease*, Fourth ed., Garland Publishing Co., New York, 1999; Roitt, I. et al., *Immunology*, (current ed.) C.V. Mosby Co., St. Louis, Mo. (1999); and also includes more recent editions of these texts.

As noted in Example VI, recent references that disclose DNA and protein immunization to induce anti-HIV-1 immunity, particularly neutralizing antibodies, include Vaine M et al., *J Virol.* 2008, 82:7369-78; Wang S et al., Vaccine. 2008, 26:1098-110; Zolla-Pazner S et al, Virology. 2008, 372:233-46; Lu S., Springer Semin Immunopathol. 2006, 28:255-65; Wang S et al, Virology. 2006, 350:34-47; Wang, S et al. *J Virol.* 2005, 79:7933-7 (incorporated by reference).

As exemplified below with Immunogen I and Immunogen II, the V3 surface constitutes 51% or 6%, respectively of the total solvent-accessible surface of the immunogen. This high proportion of V3 epitopes on the immunogen surface will result in highly focused antibody response when the immunogen is administered.

It has been suggested that immunization with an immunogen with repetitive representation of an epitope on its surface results in stronger immune responses, probably because such an immunogen can trigger oligomerization of B-cell receptors recognizing the epitope. (See, for example, Puffer E B et al., 2007, *ACS Chem. Biol.* 2:252-62.) However, the inventors do not wish to be bound by any proposed mechanism that may be involved in this process.

Combination of these features make the present immunogen uniquely capable of inducing a strong, broadly neutralizing antibody response against gp120 and thereby, generate a more effective state of immunity against HIV.

V3 Peptides for Incorporation into Scaffolds

Immunogen I, exemplified below, comprises a V3 sequence CTRPSNNTRKSIHIGPGRAFYTTGEI-IGDIRQAHC (SEQ ID NO:4). The V3-CTB construct, and, more precisely, the above V3 sequence, are referred to herein as "long" based on its length of 35 amino acids.

Immunogen II, exemplified below, includes only the V3 "crown" residues of the V3 loop, preferably KRIHIG-PGRAEYG (SEQ ID NO:6) A fragment of 10-12 residues of SEQ ID NO:6 can be used as well. The V3-CTB construct, and, more precisely, the above V3 sequence, are referred to herein as "short" based on its length of 13 amino acids.

Another "short" V3 peptide construct has the sequence .AIITFKRIHIGPGRAEYGMT (SEQ ID NO:7). This peptide comprises a "10+2" segment of V3-based sequence (bold and underscored above). The N-terminal residue from V3 ($Thr^4$) is separated from the core 10 mer by a $Phe^5$ residue. The C terminal residue of the V3 portion ($Tyr^{17}$) is separated from the core 10 mer by a $Glu^{16}$ residue. $Thr^4$ is flanked on its N-terminal side with an Ala-Ile-Ile tripeptide, and $Tyr^{17}$ is flanked on it's C-terminal side with a Gly-Met-Thr tripeptide.

Cyclic Peptides

The present invention also includes cyclic peptides that are preferably synthesized and include two Cys residues that bond via a disulfide linkage forming the cyclic peptide. Alternatively, the peptide may be cyclized by chemical means without relying upon disulfide bonding of two Cys residues, for example, by introduction of a linker.

The peptide compositions of the present invention may be synthesized using ordinary skill in the art of organic synthesis and peptide synthesis. New methods for restricting the secondary structure of peptides and proteins are highly desirable for the rational design of therapeutically useful conformationally-restricted (or "locked") pharmacophores. Examples include an analogue of eel calcitonin, [Asu$^{1,7}$]-eel calcitonin, in which α-aminosuberic acid (Asu) replaces the Cys residues at positions 1 and 7 (Morikawa, T. et al., *Experientia* 32:1104-6 (1976)). This analogue had significant biological activity, leading the authors to conclude that the disulfide bond in calcitonin is not essential for biological activity as long as the specific conformation of the peptide is maintained by an intramolecular bridge.

The purely chemical approaches for restricting secondary structure often require extensive multistep syntheses (Olson, G. L., *J. Am. Chem. Soc.* 112:323 (1990)). An alternative approach involves installing covalent bridges in peptides. However, due to the sensitivity of the peptide backbone and side chains, this method necessitates careful protection/deprotection strategies. For example, this problem occurred in the preparation of polymethylene analogues of [Arg$^8$]vasopressin Asu replaced Cys residues at positions 1 and 7 and in which the N-terminal amino group was removed (S. Hase et al., *Experientia* 25:1239-40 (1969); S. Hase et al., *J. Amer. Chem. Soc.* 94:3590 (1972)), yielding deamino-dicarba-Arg$^8$-vasopressin.

The peptide may include substitutions of residues from a "natural" V3 sequence or chemical modification of side chains or introduction other organic groups to enhance stability and antigenic/immunogenic function as described herein.

Covalent linkages can, in selected instances, be established using other chemical methods, for example, by lactam formation between carboxylic acid and amine side chains $$X^1X^2X^3X^4X^5X^6X^7...X^n$$
$$|\_\_\_\_\text{Linker}\_\_\_\_|$$

wherein n is preferably between 10 and 23 (i.e., a 10-mer to a 23-mer peptide). The linker is optional, particularly if $X^1$ and $X^n$ are each Cys. In one embodiment, all of $X^1$ through $X^n$ represent amino acids (L- or D-) corresponding to all or part of the V3 loop of the HIV-1 virus of the desired strain, or subtype consensus sequence. The present inventors prepared and analyzed a cyclic peptide from HIV-1 which is a useful "medium" size V3 crown peptide (see also, Example IV below) which is biotinylated ("bio-") at its N-terminal Ala residue the derivatized sequence of which is bio-AC TRKSIRIGRGQTFYACA (SEQ ID NO:8). The "internal" V3-derived sequence of this molecule (residues 3-17 of SEQ ID NO:8; bolded/underscored above) is TRKSIRIGRGQT-FYA. Note that this molecule has added to its internal V3 sequence, an N-terminal Ala-Cys and a C-terminal Cys-Ala. The peptide is cyclized by oxidation of the sulfhydryl groups of the two Cys residues to form a disulfide bridge. This is illustrated below for SEQ ID NO:8.

$$\text{ACTRKSIRIGRGQTFYACA}$$
$$|_____|$$

This cyclic peptide is more flexible and more broadly reactive yet is focused on V3 crown. This peptide can be placed, for example, on/in a CTB scaffold. Results shown in Example IV and Table 3) indicate that this peptide is bound strongly by a large number of mAbs reactive with V3 of subtype B and of non-B subtypes.

The general guiding principles determining the design of useful cyclic peptides are well-known in the art and are dictated by the need to maintain the Ab reactivity and immunogenicity of the V3 peptide, particularly for induction of broadly reactive, neutralizing, and preferably mucosal antibodies while enhancing its stability as well as the ability to inserted it into a desired scaffold protein without disrupting the "function" of the latter, i.e., immunogenicity and other binding characteristics of the scaffold such as the binding of recombinant V3-CTB to the glycolipid targets of CTB. In addition to testing a cyclic peptide serologically (as in the present example), it may be analyzed more extensively by structural (biophysical) techniques in solution or when bound to a characterizing broadly-reactive neutralizing mAb such as 447-52D, e.g., NMR spectroscopy or X-ray crystallographic methods. See, for example, PCT publication WO04/069863 of which one of the present inventors is a coinventor (and which is incorporated by reference in its entirety).

Reverse Peptides

Crystal structures of V3 peptides bound to antibodies 2219 and 2557 suggested that broad cross-clade neutralization can be achieved by a binding mode that is distinct from that occurring in complexes of mAb 447-52B with V3.

For these antibodies, the central GPG(Q/R) β turn motif and, in particular, the fourth residue (Q or R) play a relatively minor role in the interaction with antibody. Instead, the 3D conformational epitope is formed by a cluster of conserved residues from the C- and N-terminal β-strands of the crown ("the band"). In view of the favorable neutralization profile of these two mAbs it was conceived that focused presentation of this conformational epitope alone would elicit an effective neutralizing response.

Selective presentation of this epitope which is referred to as the "2219/2557 epitope" could was achieved by redesigning the sequence of the V3 immunogen so that it no longer presents other V3 conformational epitopes which are not desired. One way to achieve this, utilized herein, is to eliminate the "central" GPG(Q/R) β-turn motif. However, in the native V3 sequence, this motif provides an important constraint that brings the two strands of the crown "band" together in a specific configuration.

Another way to achieve the necessary conformational constraint is via the termini of the crown loop that are normally connected to the flexible stem of V3. By scanning the PDB database of protein structures for loops that could bridge the termini of the V3 crown, the present inventors identified two such "connector" sequences, Ala-Ser-Ser-Pro (residues 6-9 of SEQ ID NO:10) and Ser-Gly-Pro (residues 19-21 of SEQ ID NO:14).

A "reverse" peptide was designed by joining the two β-strands of the V3 crown via a reversed connector so that the new peptides have (from their N-terminus toward their C-terminus)

C-terminal strand-connector N-terminal strand,
This replaces the native structures
N-terminal strand-GPG(Q/R)-C-terminal strand.
These also included an added N- and C-terminal Cys residue that serve to cyclize the peptide.

Figure 2:
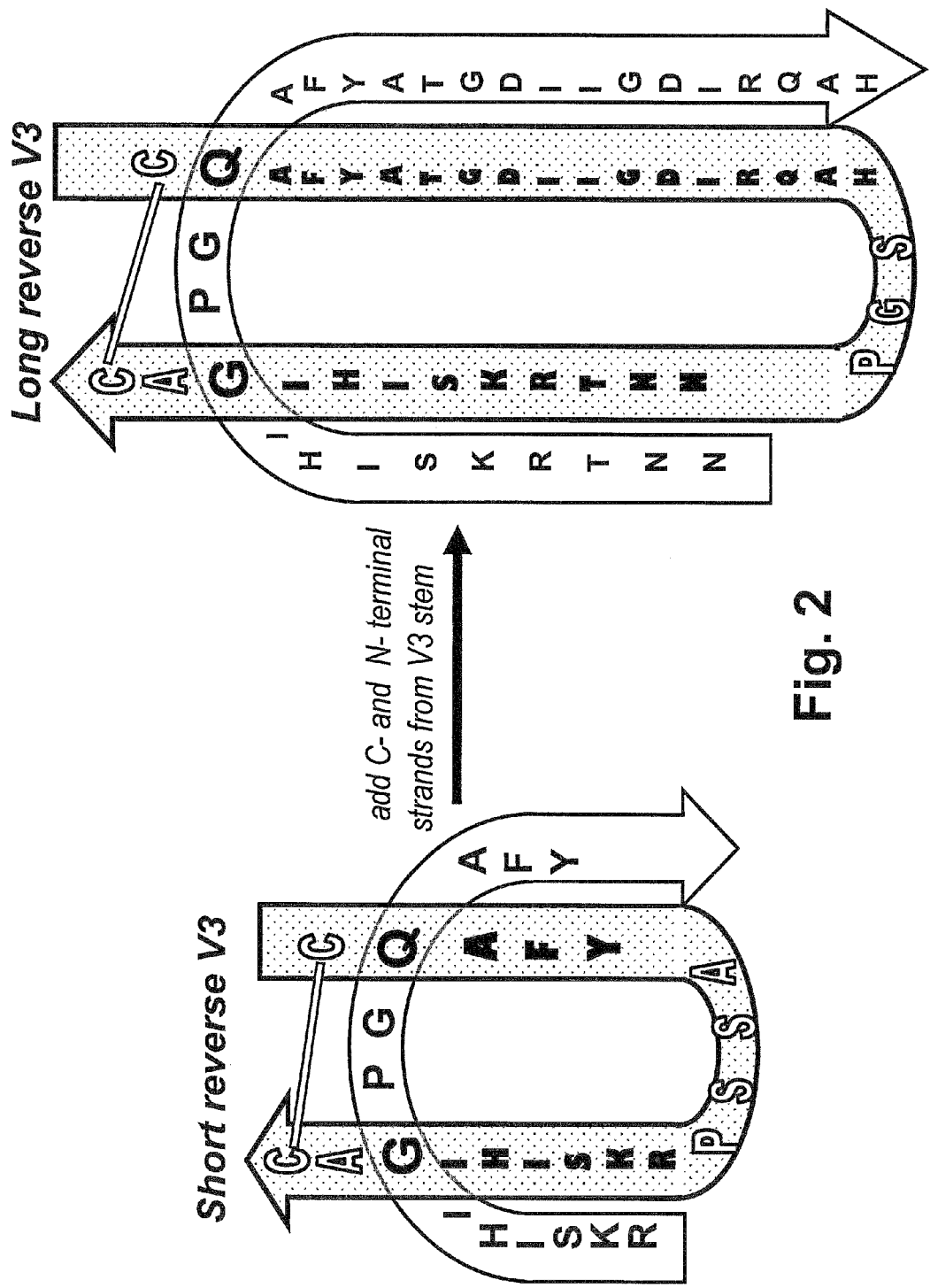
FIG. 2 is a schematic illustration of V3 "Reverse" Peptides

A schematic diagram of the "natural" V3 sequence with the reverse peptide V3 sequence overlaid are shown in FIG. 2, where the stippled "ribbon" represents the new reverse peptides. Two such peptides were made and tested, which are referred to as a "short" and "long" reverse V3 peptide.

The linear sequence of the short natural V3 peptide mimicked by the short reverse V3 peptide is NH$_2$-RKSIHIGPG QAFY-COOH (SEQ ID NO:9).

The linear sequence of the short reverse V3 peptide is NH$_2$-CQAFYASSPRKSIHIGAC-COOH (SEQ ID NO:10). The "connector" sequence is bolded and italicized above. These appear on the left side of FIG. 2. Note that the (underscored) G and Q residues of the V3 GPGQ (SEQ ID NO:11) tip in SEQ ID NO:9 are maintained in the reverse peptide but are now distant from one another (also underscored) and are respectively adjacent to, or one residue away from, the two "terminal" Cys residues.

FIG. 2 also shows in an almost "side-by-side" manner the two β-strands of V3 that flank the β-turn characterized by GPGQ (SEQ ID NO:11) (in this particular V3; GPGR (SEQ ID NO:12) in others). In the short peptide (left side of Figure) those sequences are RKSIHI and AFY (residues 1-6 and 11-13, respectively of SEQ ID NO:9 (the "original" V3 sequence).

The linear sequence of the long natural V3 peptide mimicked by the long reverse V3 peptide is NH$_2$-NNTRKSIHI GPGQAFYATGDIIGDIRQAH-COOH (SEQ ID NO:13).

The linear sequence of the long reverse V3 peptide is NH$_2$-CQAFYATGDIIGDIRQAHSGPNNTRKSIHI GAC-COOH (SEQ ID NO:14). These appear on the right side of FIG. 2. Note here that, as above, the (underscored) G and Q residues of the V3 GPGR tip in SEQ ID NO:13 are maintained in the reverse peptide but are now distant from one another (also underscored) and are respectively adjacent to, or one residue away from, the two "terminal" Cys residues.

FIG. 2 also shows in an almost "side-by-side" manner the two β-strands plus additional sequence of the V3 stem that flank the β-turn characterized here by GPGQ in the long peptide (fight side of Figure. Those sequences are NNTRK-SIHI and AFYATGDIIGDIRQAH (residues 1-9 and 14-29, respectively of SEQ ID NO:13 (the "original" V3 sequence).

A biotinylated short reverse peptide (SEQ ID NO:9) was synthesized and tested for reactivity with antibody (discussed in Example V; see Table 4). The binding profile against a panel confirmed that while this peptide does not bind to 447-52D mAb and the majority of other antibodies on the panel, it selectively interacts with 2557, 2219 and a few similar antibodies.

The same Example indicates that a biotinylated long reverse peptide (SEQ ID NO:14) was also synthesized and tested for reactivity with antibody. The binding profile against the same panel indicates a narrower range of reactivity, though where present, the reactivity was stronger. The results reveal an almost perfect relationship between human germ line immunoglobulin V region gene (VH5-51) and reactivity with these two reverse peptide antigens. There was virtually no detectable reactivity with mAbs that were not encoded by the VH5-51 variable region gene.

A construct based on the CTB scaffold and a reverse peptide was prepared as a recombinant polypeptide with the sequence:

```
                                    (SEQ ID NO:15)
TPQNITDLCA EYHNTQIHTL NDKIFSYTES LAGKREMAII

TFCQAFYASS PRKSIHIGAC ATFQVEVPGS QHIDSQKKAI

ERMKDTLRIA YLTEAKVEKLC VWNNKTPRAI AAISMAN.
```

The reverse V3 sequence in the above recombinant protein, underscored above is the "short" reverse peptide described above. Binding tests with this complex showed selective interaction with mAb 2557 (results not shown).

It is important to note that these exemplary reverse peptides can be made to mimic any of a number of natural or consensus V3 sequences of either the shorter (focused on the crown) or longer variety (extending to some stem residues). The two connector sequences described here may be introduced into a wide range of actual V3 sequences when designing the reverse peptides. Said differently, these connector peptides may have "universal" applicability in this approach.

Use of Immunogens

The present immunogen is administered by any of a number of routes known in the arg to be immunogenic, i.e., compatible with strong antibody responses. Administration may be by injection, infusion, aerosol, oral, transdermal, transmucosal, intrapleural, intrathecal, or other suitable routes. Preferably the composition is administered by intravenous, subcutaneous, intradermal, or intramuscular routes, or any combination thereof. The immunization protocol preferably includes at least one priming dose, followed by one or multiple boosting doses administered over time. An exemplary range for an immunogenically effective amount of the present immunogenic polypeptides is about 5 to about 500 μg/kg body weight. A preferred range is about 10-100 μg/kg.

Preferably, one or more unit doses of the immunogen are given at one, two or three time points. The optimal number and timing of boosts can readily be determined using routine experimentation. The immunogen may be given only as a booster, to a subject who has been primed with another form of the antigen, for example, a DNA vaccine that encodes either the V3-scaffold complex or another type of V3-endocing construct. See for example, (1) PCT publication WO 2008/005929A2, disclosing an invention by two of the present inventors (plus an additional co-inventor), that includes immunization schedules with different constructs to generate broadly-reactive neutralizing anti-gp120 antibodies; and (2) co-pending U.S. patent application Ser. No. 11/942,634 by one the present inventors). Both of these documents are incorporated by reference in their entirety. See also, Example VI and references cited therein.

Two boosts are preferred. Preferably these boosts are separated by 2 weeks, more preferably by 4 weeks, and in other embodiments, 5, 6, 8, 12 weeks, etc., as needed to achieve and maintain the desired titers and breadth of the resulting antibodies. It is common that the antibody response remains at relatively high levels for months after the last boost. Blood samples for evaluation of antibody quantity and quality is preferably obtained about 2 weeks after the final boost. Adjuvants known in the art may be used during priming, boosting or both.

In one embodiment, the present immunogenic composition is administered together with an adjuvant or other immunostimulant. Thus the immunogenic composition of this invention may further comprise one or more adjuvants or immunostimulating agents—which are preferably added to the fusion protein immunogens using for boosting the immune response. An adjuvant is any substance that can be added to an immunogen or to a vaccine formulation to enhance the immune-stimulating properties of the immunogenic moiety, such as a protein or polypeptide. Liposomes are also considered to be adjuvants. See, for example, Gregoriades, G. et al., *Immunological Adjuvants and Vaccines*, Plenum Press, New York, 1989; Michalek, S. M. et al., Liposomes as Oral Adjuvants, *Curr. Top. Microbiol. Immunol.* 146:51-58 (1989). Examples of adjuvants or agents that may add to the effectiveness of V3 DNA or peptides as immunogens include aluminum hydroxide, aluminum phosphate, aluminum potassium sulfate (alum), beryllium sulfate, silica, kaolin, carbon, water-in-oil emulsions, and oil-in-water emulsions. Other adjuvants are muramyl dipeptide (MDP) and various MDP derivatives and formulations, e.g., N-acetyl-D-glucosaminyl-(β1-4)-N-acetylmuramyl-L-alanyl-D-isoglutamine (GMDP) (Hornung, R L et al., *Ther Immunol* 1995 2:7-14) or ISAF-1 (5% squalene, 2.5% pluronic L121, 0.2% Tween 80 in phosphate-buffered solution with 0.4 mg of threonyl-muramyl dipeptide; see Kwak, L W et al., (1992) *N. Engl. J. Med.,* 327:1209-1238) and monophosphoryl lipid A adjuvant solubilized in 0.02% triethanolamine. Other useful adjuvants are, or are based on, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives such as QS21 (White, A. C. et al. (1991) *Adv.*

Exp. Med. Biol., 303:207-210) which is now in use in the clinic (Helling, F et al. (1995) Cancer Res., 55:2783-2788; Davis, T A et al. (1997) Blood, 90: 509A (abstr.)), levamisole, DEAE-dextran, blocked copolymers or other synthetic adjuvants. Examples of commercially available adjuvants include (a) Amphigen®, an oil-in-water adjuvant made of de-oiled lecithin dissolved in oil (see for example, U.S. Pat. No. 5,084,269 and US Pat Publication 20050058667A1 and (b) Alhydrogel® which is an aluminum hydroxide gel. Aluminum is approved for human use. Adjuvants are available commercially from various sources, for example, Merck Adjuvant 65® (Merck and Company, Inc., Rahway, N.J.). The immunogenic material may be adsorbed to or conjugated to beads such as latex or gold beads, ISCOMs, and the like.

The immunogenic composition may also be supplemented with an immunostimulatory cytokine, lymphokine or chemokine. Preferred cytokines are GM-CSF (granulocyte-macrophage colony stimulating factor), interleukin 1, interleukin 2, interleukin 12, interleukin 18 or interferon-γ.

General methods to prepare immunogenic pharmaceutical compositions and vaccines are described in Remington's Pharmaceutical Science; Mack Publishing Company Easton, Pa. (latest edition).

Evaluating Immune Responses when Designing and Selecting Immunogens

Advances in the field of immunology have allowed more thorough and sensitive evaluations of cellular responses to candidate HIV vaccines. Such assays as intracellular staining (e.g., flow cytometry) and ELISPOT (an enzyme-linked immunosorbent assay format), allow detecting and counting cells producing cytokines in response to antigens. For example, isolation of splenocytes or peripheral blood monocyte cells (PBMCs) from an animal or human followed by in vitro challenge with an appropriately presented HIV epitope such as V3, and finally testing by ELISPOT and/or intracellular cytokine staining (ICS), can determine the potential for a cell-mediated immune response in vaccine recipients.

Preferably ELISA and Western blots are used to assess the antibody response. These methods can assess antibody binding, antibody neutralizing capability, antibody-mediated fusion inhibition, and antibody-dependent cytotoxicity. These methods are conventional in the art and are therefore not described in any significant detail here.

An MT-2 assay can be performed to measure neutralizing antibody responses. Antibody-mediated neutralization of a selected strains or isolates of HIV-1 can be measured in an MT-2 cell-killing assay (D. Montefiori et al., 1988, J. Clin. Microbiol., 26:231-7). HIV-1$_{IIIB}$ and HIV-1$_{MN}$ induce the formation of syncytia in MT-2 T cells. The inhibition of the formation of syncytia by the sera shows the activity of neutralizing antibodies present within the sera, induced by vaccination. Immunized test and control sera can be exposed to virus-infected cells (e.g., cells of the MT-2 cell line). Neutralization can be measured by any method that determines viable cells, such as staining, e.g., with Finter's neutral red. Percentage protection can be determined by calculating the difference in absorption ($A_{540}$) between test wells (cells+virus) and dividing this result by the difference in absorption between cell control wells (cells only) and virus control wells (virus only). Neutralizing titers may be expressed, for example, as the reciprocal of the plasma dilution required to protect at least 50% of cells from virus-induced killing.

Having now generally described the invention, the same will be more readily understood through reference to the following examples which are provided by way of illustration, and are not intended to be limiting of the present invention, unless specified.

Example I

Preparation of the Recombinant CTB-Scaffold/V3-Loop Construct

Immunogen I (SEQ ID NO:3)

In this construct, the entire 35AA V3 loop (SEQ ID NO:4 is inserted into the CTB polypeptide. It is missing the N-terminal 21 residues of native CTB. The V3 loop peptide insert CTRPSNNTRKSIHIGPGRAFYTTGEIIGDIRQAHC (SEQ ID NO:4) is shown in bold italics. Three mutant (substituted) residues in the scaffold are shown as underscored below, and inserted residues are double underscored. Three residues, K, N and G, at positions 64-66 of wtCTB have been deleted. They are normally present between positions 42 and 77 of the construct below (SEQ ID NO:3) where the V3 sequence has been inserted.

```
TPQNITDLCA EYHNTQIHTL NDKIFSYTES LAGKREMAII TFCTRPSNNT    135 (SEQ ID NO: 3) {LONG}

RKSIHIGPRGR AFYTTGEIIG DIRQAHCATF QVEVPGSQHT DSQKKAIERM

KDTLRIAYLT EAKVEKLCVW NNKTPRAIAA ISMAN
```

Immunogen II (SEQ ID NO:5)

Only the V3 "crown" residues of the V3 loop, KRIHIGPGRAEYG (SEQ ID NO:6) shown as italicized and bolded below, is inserted into the CTB sequence. A fragment of 10-12 residues of SEQ ID NO:6 can be used as well. Additional mutations (substituted residues) shown as underscored are introduced to enhance conformational stability of the insert.

```
TPQNITDLCA EYHNTQIHTL NNSITSYTES LAGKREMAII TFKRIHIGPG RAEYGMTFQV  113 (SEQ ID NO: 5) {SHORT}

EVPGSQHIDS QKKAIERMKD TLRIAYLTSA KVEKLCVWNN KTPRAIAAIS MAN
```

Use of SUMO-Tagged Polypeptides

Small ubiquitin-related modifier (SUMO) is a ubiquitin-related protein that serves as a useful tag for heterologous expression. It has been fused to the N-terminus of proteins to enhanced expression and solubility of the fusion proteins. See, for example, Kim K I et al., 2002, J Cell Physiol. 191: 257-68; Zuo X et al., 2005, J Struct Funct Genomics; 6:103-11; and Butt T R et al., 2005, Protein Expr Purif 43:1-9.

Wild-type (wt) CTB (as control), Immunogen I, and Immunogen II genes were chemically synthesized and cloned into pSUMO plasmids. Amino-terminally SUMO-tagged forms of CTB, Immunogen I and Immunogen II proteins were produced by induction of T7 RNA polymerase in E. coli strain BL21(DE3) containing pSUMO-CTB, pSUMO-ImmunogenI, or pSUMO-ImmunogenII, respectively.

After adding IPTG to a log-phase culture grown in Luria-Bertani (LB) medium, the cells were pelleted, resuspended, and lysed with a French press.

SUMO-tagged CTB, Immunogen I, and Immunogen II were purified from each of the resulting cultures by affinity chromatography on a Ni-nitrilotriacetate column. SUMO tags were cleaved from the fusion proteins by a SUMO protease and removed by a Ni-NTA column. CTB, Immunogen I, and Immunogen II were collected in the flow-through and dialyzed overnight. The purified proteins were stored at −80° C.

FIG. 1 shows a Western blot that confirms the expression of Immunogens I and II. Lane 1: wtCTB; Lane 2: Immunogen 1; Lane 3: Immunogen II.

Example II

Binding of Immunogen Constructs to Human Anti-V3 Monoclonal Antibodies

Binding of the immunogen constructs to various anti-V3 human monoclonal antibodies (mAbs) from human hetero-hybridomas, was evaluated in ELISA assay (Gorny, M K et al., *J Immunol* 1997, 159:5114-22). Results are shown in Table 1, below.

Briefly, immunogen constructs at a concentration of 1 μg/ml were passively adsorbed to plastic and incubated overnight at 4° C. Controls included wild-type CTB (wt-CTB). Positive control wells were coated with a cocktail of three fusion proteins of V3 using the consensus sequence or a representative sequence of the V3 peptide loop of clade A, clade B or clade C and referred to in Table 1 as "V3-FP (ABC)". These are described in part in Gorny, M K et al., 2002, *J Virol* 76:9035-45. The V3 peptides were fused to a truncated form of MuLV gp70 (from murine leukemia virus). To represent clade B, the V3-FP(B) comprised a 263-amino-acid fragment of MuLV gp70 joined to a 45-amino-acid domain of gp120 containing the $V3_{JR-CSF}$. It was expressed in CHO cells as described in Kayman, S C et al., 1994. *J. Virol.* 68:400-10. For clade A, the V3 sequence from a clade A primary isolate 92UG037.08 was used ($V3_{92UG037}$-FP). For V3-FP(c) representing clade C, a consensus sequence from the Los Alamos National Laboratory database was used in the MuLV gp70 fusion protein. Results in Table 1 in the column labeled "V3-FP (A,B,C)" represent binding of the indicated mAbs to a cocktail of three V3 fusion proteins representing clades A, B and C.

After overnight incubation, plates were washed three times with wash buffer (1×PBS with 0.05% Tween-20. pH 7.4) before incubation for 1.5 h at 37° C. with the indicated human mAbs at a concentration of 10 μg/ml. After washing, plates were incubated with a secondary antibody, alkaline phosphatase-conjugated goat anti-human IgG (Fc specific) for another 1.5 h at 37° C. Plates were washed again and the chromogenic substrate for alkaline phosphatase, p-nitrophenyl phosphate in 10% diethanolamine, was added for 30 min. Plates were read at an absorbance of 410 nm using an automatic plate reader. Negative controls consisted of immunogen-coated wells to which an irrelevant human mAb was added (anti-parvovirus). Results appear in Table 1.

A large number of these mAbs show strong binding to Immunogen-I and Immunogen-II.

On this basis, these immunogens are expected to be potent inducers of broadly reactive anti-gp120 antibodies, including neutralizing antibodies.

TABLE 1

ANTIBODY BINDING RESULTS[a]

| | | | | Test Antigen (immobilized to Plate) | | | |
|---|---|---|---|---|---|---|---|
| mAb | Clade[b] | Ref[c] | ISOTYPE | IMMUNOGEN I | IMMUNOGEN II | V3-FP (A, B, C) | wt-CTB |
| 447-52D | B | 1 | $IgG_3\lambda$ | 2.9 | 2.9 | 2.9 | 0.1 |
| 419 | B | 2 | $IgG_1\lambda$ | 2.8 | 0.4 | 2.8 | 0.1 |
| 838 | B | 3 | $IgG_1\lambda$ | 2.9 | 0.2 | 2.8 | 0.1 |
| 1006-15D | B | 3 | $IgG_1\lambda$ | 2.8 | 2.0 | 2.9 | 0.1 |
| 1108 | B | 4 | $IgG_1\lambda$ | 2.8 | 2.8 | 2.8 | 0.1 |
| 2219 | B | 5 | $IgG_1\lambda$ | 2.8 | 1.3 | 2.8 | 0.1 |
| 2424 | B | 6 | $IgG_1\lambda$ | 2.8 | 2.8 | 2.8 | 0.1 |
| 2442 | B | 5 | $IgG_1\lambda$ | 2.9 | 2.8 | 2.9 | 0.1 |
| 694/98 | B | 1 | $IgG_1\lambda$ | 2.9 | 3.0 | 2.9 | 0.1 |
| 3527 | | n/d | | 3.0 | 3.0 | 3.0 | 0.1 |
| 1324 | E | 8 | $IgG_1\lambda$ | 0.7 | 0.2 | 3.0 | 0.1 |
| 2182 | A | 5 | $IgG_1\lambda$ | 2.9 | 2.9 | 2.9 | 0.2 |
| 2557 | AG | 7 | $IgG_1\lambda$ | 2.8 | 2.8 | 2.8 | 0.2 |
| 2601 | A | 7 | $IgG_1\lambda$ | 1.8 | 0.1 | 2.8 | 0.2 |
| 3019 | A | 7 | $IgG_1\lambda$ | 2.8 | 0.4 | 2.9 | 0.1 |
| 3074 | A1 | 7 | $IgG_1\lambda$ | 2.9 | 0.1 | 2.8 | 0.2 |
| 3694 | AG | n/d | $IgG_1\lambda$ | 2.8 | 0.4 | 2.8 | 0.1 |
| 3697 | AG | n/d | $IgG_1\lambda$ | 2.8 | 0.4 | 2.8 | 0.1 |
| 3791 | C | n/d | $IgG_1\kappa$ | 0.1 | 0.1 | 2.8 | 0.1 |
| 3792 | C | n/d | $IgG_1\lambda$ | 2.4 | 0.1 | 2.9 | 0.2 |
| 1418 (−)[d] | — | 9 | $IgG_1\lambda$ | 0.1 | 0.1 | 0.2 | 0.1 |
| 1424 (−)[d] | — | 9 | $IgG_3\lambda$ | 0.2 | 0.3 | 0.3 | 0.2 |

[a] Absorbance in arbitrary absorbance (OD) units
[b] HIV-1 clade recognized my mAb
[c] References describing mAbs
(1) Gorny, MK et al., 1992 J Virol 66:7538-42;
(2) Gorny, MK et al., 6th Ann Mtg of NCVDG for AIDS, Alexandria VA;.
(3) Gorny, MK et al., 1997, J Immunol 159:5114-22;
(4) Zolla-Pazner, S et al., 1999, J Virol 73:4042-51
(5) Gorny, MK et al., 2002, J Virol 76:9035-45;
(6) Gorny, MK et al., 2004, J Virol 78:2394-2404
(7) Gorny, MK et al., 2006, J Virol 80:6865-72;
(8) Gorny, MK et al., 1998, AIDS Res Hum Retrovir 14:213-221
(9) Gigler, A et al., 1999, J Virol 73:1974-9
[d] Anti-parvovirus mAbs (negative controls)
n/d—not described in a published document

Example III

Binding of Various V3-CTB Recombinant Polypeptides from Consensus V3 Sequences of Subtype C and H and V3 from the JRCSF HIV-1 Isolate to a Panel of V3-Specific Monoclonal Antibodies V3 loop sequences designed into mAb 447-52D like conformation on the CTB scaffold bind broadly neutralizing antibodies: Results (from ELISA assays, see above) are shown in Tables 2A-2C below. Each row shows results with a different broadly-neutralizing anti-V3 mAbs each of which was originally derived from B cells of HIV infected patients. Each value shows μg/ml of mAb bound in ELISA to the indicated antigen. >3.0 μg/ml is considered strong binding.

TABLE 2A

Antibody Binding in ELISA

| Scaffold V3 Sequence mAb | Antigen: Consensus subtype C V3 Loop Sequence Engineered onto CTB Scaffold Cholera Toxin B 'LONG' - subtype C | | | | Antigen: Consensus subtype H V3 Loop Sequence Engineered onto CTB Scaffold Cholera Toxin B 'LONG' - subtype H | | | |
|---|---|---|---|---|---|---|---|---|
| | 10.0* | 1.0 | 0.1 | 0.01 | 10.0 | 1.0 | 0.1 | 0.01 |
| Non-B seq | | | | | | | | |
| 2182 | 0.8 | 0.4 | 0.2 | 0.1 | 2.7 | 1.2 | 0.3 | 0.2 |
| 2557 | 2.6 | 2.7 | 2.5 | 0.6 | 2.7 | 2.7 | 2.4 | 0.8 |
| 2558 | 2.8 | 2.8 | 2.3 | 0.5 | 2.8 | 2.7 | 2.8 | 2.5 |
| 2601 | 2.7 | 2.7 | 0.9 | 0.2 | 2.8 | 2.7 | 2.7 | 1.5 |
| 3019 | 2.8 | 2.8 | 2.7 | 0.8 | 2.8 | 2.8 | 2.8 | 2.4 |
| 3074 | 2.8 | 2.7 | 2.5 | 0.6 | 2.7 | 2.7 | 2.7 | 1.8 |
| 3694 | 2.7 | 2.7 | 2.7 | 0.8 | 2.8 | 2.7 | 2.7 | 1.6 |
| 3697 | 2.8 | 2.8 | 2.7 | 0.7 | 2.8 | 2.8 | 2.8 | 2.4 |
| 3791 | 2.9 | 2.9 | 2.8 | 0.8 | 2.8 | 2.1 | 0.9 | 0.4 |
| 3792 | 2.9 | 1.7 | 0.3 | 0.2 | 3.0 | 2.8 | 1.0 | 0.3 |
| 3869 | 3.0 | 2.9 | 2.9 | 1.0 | 2.9 | 3.0 | 2.7 | 2.4 |
| 3881 | 3.1 | 3.0 | 3.1 | 1.3 | 3.1 | 3.1 | 3.1 | 2.2 |
| 3904 | 2.9 | 2.8 | 2.6 | 0.7 | 2.9 | 2.8 | 2.8 | 1.7 |
| 3906 | 3.1 | 3.1 | 2.5 | 0.6 | 1.2 | 0.8 | 0.4 | 0.2 |
| B-derived | | | | | | | | |
| 257 | 2.7 | 2.2 | 0.6 | 0.2 | 2.7 | 2.7 | 2.7 | 1.5 |
| 391-95 | 2.7 | 2.6 | 2.2 | 0.9 | 2.7 | 2.6 | 2.5 | 0.9 |
| 419 | 2.8 | 2.8 | 2.4 | 0.7 | 2.7 | 2.3 | 0.6 | 0.2 |
| 447 | 2.7 | 2.7 | 2.6 | 1.1 | 2.7 | 2.7 | 2.5 | 1.1 |
| 694/98 | 2.1 | 0.6 | 0.3 | 0.2 | 2.8 | 2.7 | 2.7 | 1.5 |
| 2456 | 2.7 | 2.7 | 2.6 | 0.9 | 2.7 | 2.7 | 2.6 | 1.4 |
| 1006-15D | 2.7 | 2.7 | 2.7 | 2.0 | 2.7 | 2.7 | 2.7 | 1.9 |
| 2191 | 2.8 | 2.8 | 2.8 | 1.9 | 2.5 | 0.9 | 0.3 | 0.2 |
| 2219 | 2.9 | 2.9 | 2.9 | 1.5 | 2.8 | 2.8 | 2.8 | 2.3 |
| 2442 | 2.9 | 2.9 | 2.5 | 0.7 | 2.9 | 2.9 | 2.8 | 2.2 |

*mAb conc, μg/ml, in ELISA wells

Color code:

Black >3.1,

Gray: 2-3;

White 0-1.9

TABLE 2B

Antibody Binding in ELISA

| Scaffold V3 Sequence mAb | Antigen: JRCSF strain* V3 Loop Sequence on CTB Scaffold Cholera Toxin B JRCSF LONG | | | | Antigen: JRCSF strain V3 Loop Constrained Sequence** on CTB Scaffold Cholera Toxin B JRCSF SHORT | | | |
|---|---|---|---|---|---|---|---|---|
| | 10.0+ | 1.0 | 0.1 | 0.01 | 10.0 | 1.0 | 0.1 | 0.01 |
| Non-B seq | | | | | | | | |
| 2182 | 2.8 | 2.8 | 2.6 | 2.0 | 2.7 | 2.8 | 2.7 | 1.5 |
| 2557 | 2.6 | 2.7 | 2.4 | 1.7 | 2.6 | 2.2 | 1.3 | 0.4 |
| 2558 | 2.8 | 2.7 | 2.1 | 1.3 | 2.6 | 1.5 | 0.7 | 0.2 |
| 2601 | 0.2 | 0.1 | 0.1 | 0.1 | 0.1 | 0.1 | 0.1 | 0.1 |
| 3019 | 2.7 | 2.6 | 1.8 | 1.0 | 0.4 | 0.2 | 0.1 | 0.1 |
| 3074 | 2.6 | 2.1 | 1.4 | 0.8 | 0.2 | 0.2 | 0.1 | 0.1 |
| 3694 | 2.7 | 2.2 | 1.3 | 0.7 | 0.8 | 0.4 | 0.1 | 0.1 |
| 3697 | 2.7 | 2.5 | 1.8 | 1.2 | 0.5 | 0.2 | 0.1 | 0.1 |
| 3791 | 0.1 | 0.1 | 0.1 | 0.1 | 0.2 | 0.1 | 0.1 | 0.1 |
| 3792 | 2.3 | 1.3 | 0.4 | 0.2 | 0.2 | 0.1 | 0.1 | 0.1 |
| 3869 | 2.4 | 2.0 | 1.1 | 0.6 | 0.2 | 0.1 | 0.1 | 0.1 |
| 3881 | 0.4 | 0.1 | 0.1 | 0.1 | 0.2 | 0.1 | 0.1 | 0.1 |
| 3904 | 0.1 | 0.2 | 0.1 | 0.1 | 0.1 | 0.1 | 0.1 | 0.1 |
| 3906 | 0.4 | 0.2 | 0.1 | 0.1 | 0.1 | 0.1 | 0.1 | 0.1 |
| B-derived | | | | | | | | |
| 257 | 2.8 | 2.7 | 2.3 | 0.9 | 1.9 | 0.8 | 0.3 | 0.2 |
| 391-95 | 2.6 | 2.6 | 2.3 | 1.2 | 2.6 | 2.5 | 2.6 | 1.5 |
| 419 | 2.6 | 2.0 | 0.9 | 0.2 | 0.4 | 0.2 | 0.1 | 0.2 |
| 447 | 2.7 | 2.7 | 2.4 | 1.2 | 2.7 | 2.7 | 2.4 | 0.8 |
| 694/98 | 2.6 | 2.4 | 1.7 | 0.6 | 2.7 | 2.7 | 2.2 | 0.7 |
| 2456 | 2.5 | 2.2 | 1.4 | 0.5 | 0.3 | 0.2 | 0.1 | 0.1 |
| 1006-15D | 2.6 | 2.4 | 2.3 | 1.4 | 1.7 | 0.7 | 0.3 | 0.1 |
| 2191 | 2.6 | 2.6 | 2.1 | 1.0 | 0.5 | 0.3 | 0.2 | 0.1 |
| 2219 | 2.7 | 2.7 | 2.2 | 1.2 | 1.6 | 0.5 | 0.3 | 0.2 |
| 2442 | 2.7 | 2.5 | 2.0 | 0.9 | 2.7 | 2.8 | 2.5 | 0.8 |

*JRSCF is a subtype B strain (group M) with a V3 sequence very similar to the consensus subtype B sequence.
**Antigen was structurally designed to constrain the V3 loop to a conformation resembling mAb 447-bound antigen. This peptide was engineered onto the CTB scaffold. As expected this construct binds only 447 and very few other antibodies.
+μg/ml mAb

TABLE 2C

Antibody Binding in ELISA to "Control" Antigen- CTB Protein Scaffold Alone

| Scaffold V3 Sequence mmAb | Control Antigen: CTB Protein (Scaffold) Alone Cholera toxin B none | | | |
|---|---|---|---|---|
| | 10.0* | 1.0 | 0.1 | 0.01 |
| Non-B seq | | | | |
| 2182 | 0.1 | 0.1 | 0.1 | 0.1 |
| 2557 | 0.1 | 0.1 | 0.1 | 0.1 |
| 2558 | 0.1 | 0.1 | 0.1 | 0.1 |
| 2601 | 0.1 | 0.1 | 0.1 | 0.1 |
| 3019 | 0.1 | 0.1 | 0.1 | 0.1 |
| 3074 | 0.1 | 0.1 | 0.1 | 0.1 |
| 3694 | 0.1 | 0.1 | 0.1 | 0.1 |
| 3697 | 0.1 | 0.1 | 0.1 | 0.1 |
| 3791 | 0.1 | 0.1 | 0.1 | 0.1 |
| 3792 | 0.1 | 0.1 | 0.1 | 0.1 |
| 3869 | 0.1 | 0.1 | 0.1 | 0.1 |
| 3881 | 0.1 | 0.1 | 0.1 | 0.1 |
| 3904 | 0.1 | 0.1 | 0.1 | 0.1 |
| 3906 | 0.1 | 0.1 | 0.1 | 0.2 |

TABLE 2C-continued

Antibody Binding in ELISA to "Control" Antigen-
CTB Protein Scaffold Alone

Control Antigen: CTB Protein (Scaffold) Alone

| Scaffold V3 Sequence mmAb | Cholera toxin B none | | | |
|---|---|---|---|---|
| | 10.0* | 1.0 | 0.1 | 0.01 |
| B-derived | | | | |
| 257 | 0.1 | 0.1 | 0.1 | 0.1 |
| 391-95 | 0.1 | 0.1 | 0.1 | 0.1 |
| 419 | 0.1 | 0.1 | 0.1 | 0.1 |
| 447 | 0.1 | 0.1 | 0.1 | 0.1 |
| 694-98 | 0.1 | 0.1 | 0.1 | 0.1 |
| 2456 | 0.1 | 0.1 | 0.1 | 0.1 |
| 1006-15D | 0.1 | 0.1 | 0.1 | 0.1 |
| 2191 | 0.1 | 0.1 | 0.1 | 0.1 |
| 2219 | 0.1 | 0.1 | 0.1 | 0.1 |
| 2442 | 0.1 | 0.1 | 0.1 | 0.1 |

*mAb conc, μg/ml, in ELISA wells

Example IV

Binding of Various V3 Cyclic and Linear Peptides to Panel of V3-Specific mAbs Binding of a "medium"-sized synthetic cyclic V3 peptide and a "short" linear V3 peptide to a panel of mAbs was tested in ELISA (See Examples I-II). Results appear in Table 3. Reactivity with the cyclic peptide was markedly greater. The cyclic peptide is more flexible, more broadly reactive yet was focused on V3 crown. This peptide can be placed on CTB to yield an improved immunogen.

TABLE 3

Binding of Cyclic Biotinylated V3 Peptide to Ab Panel.

| | Linear Peptide Antigen: AllTFKRIHIGPGRAEYGMT SEQ ID NO: 7 | | | | Cyclic Peptide Antigen: bio-ACTRKSIRIGRGQTFYACA (SEQ ID NO: 8) | | | |
|---|---|---|---|---|---|---|---|---|
| mAb | 10* | 1 | 0.1 | 0.01 | 10 | 1 | 0.1 | 0.01 |
| 2182 | 0.1 | 0.1 | 0.1 | 0.1 | 0.1 | 0.1 | 0.1 | 0.1 |
| 2557 | 2.4 | 2.5 | 2.5 | 1.0 | 2.5 | 2.6 | 2.5 | 0.46 |
| 2558 | 0.7 | 0.3 | 0.2 | 0.1 | 2.6 | 2.8 | 2.6 | 2.4 |
| 2601 | 0.1 | 0.1 | 0.1 | 0.1 | 1.2 | 0.2 | 0.12 | 0.1 |
| 3019 | 2.4 | 2.6 | 2.6 | 1.7 | 2.5 | 2.8 | 2.5 | 0.4 |
| 3074 | 0.1 | 0.1 | 0.11 | 0.1 | 2.5 | 2.7 | 2.6 | 1.9 |
| 3694 | 0.1 | 0.1 | 0.1 | 0.1 | 2.6 | 2.7 | 2.7 | 2.2 |
| 3697 | 0.1 | 0.1 | 0.1 | 0.2 | 2.6 | 2.7 | 2.0 | 0.3 |
| 3791 | 0.1 | 0.12 | 0.1 | 0.1 | 2.7 | 2.8 | 2.8 | 1.8 |
| 3792 | 0.1 | 0.1 | 0.12 | 0.1 | 2.0 | 0.3 | 0.1 | 0.1 |
| 3869 | 0.1 | 0.1 | 0.1 | 0.1 | 2.7 | 2.9 | 2.8 | 2.4 |
| 3881 | 0.1 | 0.1 | 0.1 | 0.1 | 2.8 | 2.9 | 2.9 | 2.1 |
| 3904 | 0.1 | 0.1 | 0.1 | 0.1 | 2.5 | 2.5 | 2.5 | 0.8 |
| 3906 | 0.1 | 0.1 | 0.1 | 0.1 | 2.5 | 2.4 | 2.4 | 0.4 |
| 257 | 2.5 | 1.4 | 0.2 | 0.1 | 0.2 | 0.1 | 0.1 | 0.1 |
| 391-95 | 0.1 | 0.1 | 0.1 | 0.1 | 1.6 | 0.4 | 0.1 | 0.1 |
| 419 | 2.5 | 2.0 | 0.4 | 0.1 | 2.6 | 2.6 | 2.7 | 0.7 |
| 447 | 0.1 | 0.1 | 0.1 | 0.2 | 2.6 | 2.6 | 2.6 | 2.3 |
| 694/98 | 0.1 | 0.1 | 0.1 | 0.1 | 0.1 | 0.1 | 0.1 | 0.1 |
| 2456 | 2.3 | 0.4 | 0.1 | 0.1 | 2.7 | 2.7 | 1.7 | 0.3 |
| 1006-15D | 2.6 | 2.6 | 2.7 | 1.7 | 2.8 | 2.8 | 2.8 | 0.9 |
| 2191 | 0.1 | 0.1 | 0.1 | 0.1 | 2.8 | 2.9 | 2.8 | 1.3 |
| 2219 | 2.6 | 1.3 | 0.2 | 0.1 | 2.8 | 2.8 | 2.2 | 0.2 |
| 2442 | 0.1 | 0.1 | 0.1 | 0.1 | 2.9 | 2.9 | 2.9 | 1.7 |

(Legend for Table 3)
*mAb conc, μg/ml, in ELISA wells
Cyclic biotinylated peptide bio-ACTRKSIRIGRGQTFYACA (SEQ ID NO: 8) includes the (underscored) V3 residues. TRKSIRIGRGQTFYA (residues 3-17 of SEQ ID NO: 8).
Short V3 Linear peptide. AllTFKRIHIGPGRAEYGMT (SEQ ID NO: 7) includes 10 +2 V3 residues separated as shown above where the V3-derived residues are underscored.
Color coding:
Black is >2.
Gray is 1-2;
White - <1

Example V

Design of Reverse V3 Peptides and Their Binding to Anti-V3 mAbs

The rationale for, and approach to, designing novel "reverse" V3 peptides was discussed above. These peptides were intended to omit those positions in β turns that are not important for interaction with antibody while preserving the β-strands adjacent to the GPG(Q/R) turn with a novel "connector" sequence that was introduced at the opposite ends of the β-strands.

These structures were designed to present conformational epitopes that are recognized by neutralizing mAbs 2557 and 2219 in a more focused manner so that they would elicit broadly-reactive neutralizing antibodies when used as immunogens/vaccines.

Design of two such peptides and their sequences are shown in FIG. 2. By scanning the PDB database of protein structures for loops that could bridge the termini of the V3 crown, the present inventors identified two such "connector" sequences, Ala-Ser-Ser-Pro (residues 6-9 of SEQ ID NO:10) and Ser-Gly-Pro (residues 19-21 of SEQ ID NO:14). A "reverse" peptide was designed by joining the two β-strands of the V3 crown via a reversed connector so that the new peptides have (from their N-terminus toward their C-terminus):

C-terminal strand-connector-N-terminal strand,
This replaces the native structure:
N-terminal strand-GPG(Q/R)-C-terminal strand.

These also included an added N- and C-terminal Cys residue that serve to cyclize the peptide.

The linear sequence of the short natural V3 peptide mimicked by the short reverse V3 peptide is NH$_2$-RKSIHIGPGQAFY-COOH (SEQ ID NO:9). The linear sequence of the short reverse V3 peptide is NH$_2$-CQAFYASSPRKSIHIGAC-COOH (SEQ ID NO:10). The "connector" sequence is bolded and italicized above. These appear on the left side of FIG. 2. Note that the (underscored) G and Q residues of the V3 GPGQ (SEQ ID NO:11) tip in SEQ ID NO:9 are maintained in the reverse peptide but are now distant from one another (also underscored) and are respectively adjacent to, or one residue away from, the two "terminal" Cys residues.

FIG. 2 also shows in an almost "side-by-side" manner the two β-strands of V3 that flank the β-turn characterized by GPGQ (SEQ ID NO:11) (in this particular V3; GPGR (SEQ ID NO:12) in others). In the short peptide (left side of Figure) those sequences are RKSIHI and AFY (residues 1-6 and 11-13, respectively of SEQ ID NO:9 (the "original" V3 sequence).

The linear sequence of the long natural V3 peptide mimicked by the long reverse V3 peptide is NH₂-NNTRKSIHI GPGQAFYATGDIIGDIRQAH-COOH (SEQ ID NO:13).

The linear sequence of the long reverse V3 peptide is NH₂-CQAFYATGDIIGDIRQAHSGPNNTRKSIHI GAC-COOH (SEQ ID NO:14). These appear on the right side of FIG. 2. Note here that, as above, the (underscored) G and Q residues of the V3 GPGR tip in SEQ ID NO:13 are maintained in the reverse peptide but are now distant from one another (also underscored) and are respectively adjacent to, or one residue away from, the two "terminal" Cys residues.

FIG. 2 also shows in an almost "side-by-side" manner the two β-strands plus additional sequence of the V3 stem that flank the β-turn characterized here by GPGQ in the long peptide (fight side of Figure. Those sequences are NNTRK-SIHI and AFYATGDIIGDIRQAH (residues 1-9 and 14-29, respectively of SEQ ID NO:13 (the "original" V3 sequence).

A biotinylated short reverse peptide (SEQ ID NO:9) was synthesized and tested for reactivity with antibody as shown in Table 4, below. The binding profile against a panel confirmed that while this peptide does not bind to 447-52D mAb and the majority of other antibodies on the panel, it selectively interacts with 2557, 2219 and a few similar antibodies.

A biotinylated long reverse peptide (SEQ ID NO:14) was also synthesized and tested for reactivity with antibody. The binding profile against the same panel indicates a narrower range of reactivity, though where present, the reactivity was stronger. The results reveal an almost perfect relationship between human germ line immunoglobulin V region gene (VH5-51) and reactivity with these two reverse peptide antigens. There was virtually no detectable reactivity with mAbs that were not encoded by the VH5-51 variable region gene.

A construct based on the CTB scaffold and a reverse peptide was prepared as a recombinant polypeptide with the sequence:

(SEQ ID NO:15)
TPQNITDLCA EYHNTQIHTL NDKIFSYTES LAGKREMAII

TFCQAFYASS PRKSIHIGAC ATFQVEVPGS QHIDSQKKAI

ERMKDTLRIA YLTEAKVEKLC VWNNKTPRAI AAISMAN.

The reverse V3 sequence in the above recombinant protein, underscored above is the "short" reverse peptide described above. Binding tests with this complex showed selective interaction with mAb 2557 (results not shown).

TABLE 4

Reverse V3 Peptide: A VH5-51-specific Antigen

| VH5-51 mAbs | | Non CH5-51 mAbs | |
|---|---|---|---|
| mAb | Titer | mAb | Titer |
| 2557 | 3.9 | 1108 | 0.0 |
| 2558 | 1.8 | 1334 | 0.1 |
| 838 | 3.4 | 453 | 0.1 |
| 1006-15 | 3.7 | 268 | 0.1 |
| 2219 | 3.6 | 386 | 0.1 |
| 908 | 3.5 | 2182 | 0.1 |

TABLE 4-continued

Reverse V3 Peptide: A VH5-51-specific Antigen

| VH5-51 mAbs | | Non CH5-51 mAbs | |
|---|---|---|---|
| mAb | Titer | mAb | Titer |
| 257 | 3.8 | 391-95 | 0.1 |
| 782 | 3.5 | 2442 | 0.1 |
| 419 | 3.5 | 447 | 0.1 |
| 3019 | 3.7 | 694/98 | 0.1 |
| 2456 | 3.2 | 2424 | 0.1 |
| 2483 | 3.4 | 2412 | 0.1 |
| 4022 | 3.0 | 537 | 0.1 |
| 3792 | 3.5 | 418 | 0.1 |
| 3694 | 0.1 | 504 | 0.1 |
| 3906 | 0.1 | 311 | 0.1 |
| 4025 | 0.1 | 412 | 0.1 |
| 4085 | 0.1 | 1027-15 | 0.5 |
| | | 2191 | 0.1 |
| | | 3697 | 0.1 |
| | | 3074 | 0.1 |
| | | 3881 | 0.1 |
| | | 3869 | 0.1 |
| | | 2601 | 0.1 |
| | | 3904 | 0.1 |
| | | 3791 | 0.1 |
| | | 1324E | 0.1 |

Example VI

Immunization of Subjects with HIV-1 Subtype B V3-CTB Protein Complexes Induces Broadly Reactive Neutralizing Antibodies For detailed description of methods of DNA and protein immunization against HIV-1 for generating neutralizing antibody responses, see publications by co-inventor Shan Lu and his colleagues (including other present coinventors), for example, Vaine M et al., J Virol. 2008, 82:7369-78; Wang S et al., Vaccine. 2008, 26:1098-110; Zolla-Pazner S et al, Virology. 2008, 372:233-46; Lu S., Springer Semin Immunopathol. 2006, 28:255-65; Wang S et al, Virology. 2006, 350: 34-47; Wang, S et al. J Virol. 2005, 79:7933-7.

Female New Zealand rabbits (2 kg) received three immunizations with DNA expression vectors expressing gp120 protein of the JR-FL strain of HIV-1 and codon-optimized for expression in rabbit cells. DNA was adsorbed to gold particles and administered intradermally via gene gun at times 0, 2 weeks and 4 weeks. Each shot delivered 1 μg of DNA and a total of 36 non-overlapping shots were delivered to each rabbit at each of the three time points at the surface of shaved abdominal skin after animals are anesthetized according to IACUC approved protocols. Thus, the total dose per prime was 36 μg DNA.

Each animal received 100 μg of DNA distributed in non-overlapping sites on the surface of shaved abdominal skin after anesthesia according to IACUC approved protocols. Pre-immunization serum samples were collected immediately before the first priming immunization.

Six weeks after the last priming dose, rabbits were given booster immunizations with 36 μg of the indicated proteins (various V3-CTB complexes) followed by another boost 4 weeks later. Two weeks after the last boost, serum samples were obtained by venipuncture.

For further description of this method of immunization, see publications from co-inventor Shan Lu and his colleagues including some present coinventors, for example, Vaine M et al., J Virol. 2008, 82:7369-78; Wang S et al., Vaccine. 2008, 26:1098-110; Zolla-Pazner S et al, Virology.

2008, 372:233-46; Lu S., Springer Semin Immunopathol. 2006, 28:255-65; Wang S et al, Virology. 2006, 350:34-47; Wang, S et al. *J Virol.* 2005, 79:7933-7.

Sera were tested in neutralization assays against pseudoviruses with V3 consensus sequence from various subtypes to test strength and breadth of the response, showing geometric mean titers. Stronger responses are reflected in 90% neutralization titers (vs. 50%), which are the dilutions resulting in 90% (or 50% neutralization. Results appear in Table 5.

The same sera were tested in neutralization assays against primary HIV-1 isolates, a more rigorous test of the neutralizing capacity of the antibodies. The latter was expressed as the serum dilution resulting in an $IC_{50}$ (inhibitory concentration resulting in 50% neutralization, as above). Positive rabbits are indicted and geometric mean titers (of positive sera only; gray boxes) are shown in Table 6. The "long" V3 peptide inserted in CTB (SEQ ID NO:5) gave much broader and more potent responses than the short form of V3 (SEQ ID NO:3), both in neutralization of pseudoviruses and of primary viral isolates.

TABLE 5

Neutralizing Titers of Rabbit Antisera for V3 Chimeric Pseudoviruses
(Geometric mean 50% and 90% neutralizing titers

| Priming DNA | Boost Protein | rabbit # | B | F | A/E | A1 | A/G | H | C |
|---|---|---|---|---|---|---|---|---|---|
| $IC_{50}$ (1/serum dilution) | | | | | | | | | |
| JR-FL.opt | Subtype B-V3-consensus Seq (Short) on CTB | 68 | 316 | <10 | <10 | <10 | <10 | <10 | <10 |
| | | 69 | 332 | 8 | <10 | 21 | <10 | <10 | <10 |
| | | 70 | 410 | <10 | <10 | <10 | <10 | <10 | <10 |
| | | 71 | 1,638 | 9 | 16 | 31 | <10 | <10 | <10 |
| | | 72 | 512 | <10 | 7 | <10 | <10 | <10 | <10 |
| JR-FL.opt | Subtype B-V3-consensus Seq (Long) on CTB | 73 | 24,970 | 34 | 56 | 32 | <10 | <10 | <10 |
| | | 74 | 64,250 | 820 | 159 | 620 | 1,022 | 17 | 209 |
| | | 75 | 37,987 | 613 | 648 | 296 | 190 | 24 | 67 |
| | | 76 | 8,521 | 124 | 33 | 130 | 53 | 10 | 22 |
| | | 77 | 50,912 | 1,022 | 559 | 686 | 317 | 111 | 104 |
| $IC_{90}$ (1/serum dilution) | | | | | | | | | |
| JR-FL.opt | Subtype B-V3-consensus Seq (Short) on CTB | 68 | 39 | <10 | <10 | <10 | <10 | <10 | <10 |
| | | 69 | 46 | <10 | <10 | <10 | <10 | <10 | <10 |
| | | 70 | 63 | <10 | <10 | <10 | <10 | <10 | <10 |
| | | 71 | 164 | <10 | <10 | <10 | <10 | <10 | <10 |
| | | 72 | 40 | <10 | <10 | <10 | <10 | <10 | <10 |
| JR-FL.opt | Subtype B-V3-consensus Seq (Long) on CTB | 73 | 3,168 | <10 | <10 | <10 | <10 | <10 | <10 |
| | | 74 | 3,776 | 166 | 20 | 88 | 109 | <10 | 23 |
| | | 75 | 3,521 | 60 | 72 | 51 | 28 | <10 | <10 |
| | | 76 | 1,967 | 23 | <10 | 12 | <10 | <10 | <10 |
| | | 77 | 3,550 | 128 | 119 | 72 | 41 | 13 | 7 |

Color coding:

Black: >1000;

Gray: 10-1000;

White: <10-100

TABLE 6

Neutralizing Titers of Rabbit Antisera for Primary HIV-1 Isolates
(Geometric mean 50% neutralizing titer

| Priming Immunogen/Boosting Immunogen | Rabbit # | CLADE B | | | CLADE A | | | |
|---|---|---|---|---|---|---|---|---|
| | | BX08 | BZ167 | CA5 | NYU3738 | VI191 | VI313 | CA1 |
| DNA: Clade B/V3 Protein: Clade B Short - CTB | 68 | | | | | | | |
| | 69 | | 18 | | | | | |
| | 70 | | | | | | 10 | |
| | 71 | | | | | | | |
| | 72 | | | | | | | |
| DNA: Clade B/V3 Protein: Clade B Long - CTB | 73 | | | | | | | |
| | 74 | | | | | | 31 | 14 |
| | 75 | 44 | 113 | | | | | |
| | 76 | | | 21 | | | | |
| | 77 | | | | | | | |

TABLE 6-continued

Neutralizing Titers of Rabbit Antisera for Primary HIV-1 Isolates
(Geometric mean 50% neutralizing titer

| | | CLADE A/G | | | CLADE C | | | | |
|---|---|---|---|---|---|---|---|---|---|
| | | DJ263 | NYU6525 (2) | NY129(5) | 97ZA009 | 98CN006 | 92BR025 | 93MW965 | 93MW960 |
| DNA: Clade B/V3 Protein: Clade B Short - CTB | 68 | | | | | | | | |
| | 69 | | | | | | | | |
| | 70 | | | | | | | | |
| | 71 | | | | | | | | |
| | 72 | | | | | | | | |
| DNA: Clade B/V3 Protein: Clade B Long - CTB | 73 | | | | | | | | |
| | 74 | | | | | | | | |
| | 75 | 75 | | | | | | | |
| | 76 | | | | | | | | |
| | 77 | | | | | | | | |

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A recombinant immunogenic polypeptide comprising a cyclic V3 loop peptide of the HIV gp120 protein or a cyclic reverse V3 loop peptide, inserted into an immunogenic scaffold protein, wherein (a) the immunogenic scaffold protein is (i) cholera toxin subunit B (CTB) of sequence SEQ ID NO:1, (ii) a variant of SEQ ID NO:1 in which the amino acid residue at position 115 is Arg; or (b) residues 64-66 of (i) said CTB (SEQ ID NO:1), or (ii) said variant of SEQ ID NO:1 are deleted and replaced by the V3 loop peptide or the reverse V3 loop peptide, (c) the recombinant polypeptide with said V3 loop peptide inserted continues to bind to GM1 ganglioside oligosaccharide structure,

37

(d) the V3 loop peptide in said scaffold protein is cyclic and has a conformation that is recognized by, and bound by, a broadly neutralizing anti-HIV-1 antibody; and
(e) said recombinant polypeptide is immunogenic, inducing a broadly-neutralizing cross-clade anti-V3 antibody response in a subject primed against a V3 epitope, which neutralizes heterologous HIV-1 viruses.

2. The immunogenic polypeptide of claim 1, wherein the V3 loop peptide is said reverse peptide which is organized to include, in the order N-terminal to C terminal:
(i) a β strand sequence of the V3 C terminal region,
(ii) a connector peptide, and
(iii) a β strand sequence of the V3 N terminal region.

3. An immunogenic pharmaceutical composition comprising the immunogenic polypeptide of claim 1 and an immunologically and pharmaceutically acceptable vehicle or excipient.

4. An immunogenic pharmaceutical composition comprising the immunogenic polypeptide of claim 2 and an immunologically and pharmaceutically acceptable vehicle or excipient.

5. A method for inducing a broadly neutralizing, cross-clade antibody response against a V3 epitope of HIV-1 gp120 in a subject in need thereof who has been primed against a V3 epitope, comprising administering to the subject an effective amount of the immunogenic polypeptide according to claim 1, wherein the response results in antibodies that neutralize HIV-1 viruses heterologous to the virus strain or clade from which the immunogenic polypeptide was derived.

6. A method for inducing a broadly neutralizing, cross-clade antibody response against a V3 epitope of HIV-1 gp120 in a subject in need thereof who has been primed against a V3 epitope, comprising administering to the subject an effective amount of the immunogenic polypeptide according to claim 2, wherein the response results in antibodies that neutralize HIV-1 viruses heterologous to the virus strain or subtype from which the immunogenic polypeptide was derived.

7. A kit comprising in separate compartments in close proximity therein:
(a) one or more unit doses of the immunogenic polypeptide of claim 1, and
(b) instructions for administering the immunogenic polypeptide or composition to a subject for inducing said broadly-neutralizing antibody response.

8. A recombinant immunogenic polypeptide comprising a cyclic V3 loop peptide, of the HIV gp120 protein, or a cyclic reverse V3 loop peptide inserted into the sequence of a scaffold protein, wherein:
(a) the V3 loop peptide is:
(i) CTRPSNNTRKSIHIGPGRAFYTTGEI-IGDIRQAHC (SEQ ID NO:4); or
(ii) a corresponding V3 loop peptide from an HIV-1 virus clade or a clade's consensus V3 sequence, which clade is clade B, clade C, or clade H, or
(iii) a V3 loop peptide from HIV-1 strain JRCF,
(b) the sequence of the reverse V3 loop peptide is
(i) CQAFYASSPRKSIHIGAC (SEQ ID NO:10) or
(ii) CQAFYATGDIIGDIRQAHSGPNNTRKSIHIGAC (SEQ ID NO:14)
(c) the immunogenic scaffold protein is
a variant of CTB (SEQ ID NO:1) that differs only at position 115 and has only the CTB-derived residues: TPQNITDLCAEYHNTQIHTLNDKIF-SYTESLAGKREMAIITFATFQVEVP GSQHID-SQKKAIERMKDTLRIAYLTEAKVEKL-CVWNNKTPRAIAAISMAN which are residues 1-42 and 78-135 of SEQ ID NO:3, or

38 wherein, the sequence of the recombinant immunogenic polypeptide is
(A) TPQNITDLCA EYHNTQIHTL NDKIFSYTES LAGKREMAII TFCTRPSNNT RKSIHIGPGR AFYTTGEIIG DIRQAHCATF QVEVPGSQHI DSQKKAIERM KDTLRIAYLT EAKVEKL-CVW NNKTPRAIAA ISMAN (SEQ ID NO:3), or
(B) TPQNITDLCA EYHNTQIHTL NDKIFSYTES LAGKREMAII TFCQAFYASS PRKSIHIGAC ATFQVEVPGS QHIDSQKKAI ERMKDTLRIA YLTEAKVEKL CVWNNKTPRA IAAISMAN (SEQ ID NO:15).

9. The recombinant immunogenic polypeptide of claim 8, the sequence of which is SEQ ID NO:3.

10. The recombinant immunogenic polypeptide of claim 8, the sequence of which is SEQ ID NO:15.

11. The recombinant immunogenic polypeptide of claim 8, which comprises the cyclic reverse V3 loop peptide the sequence of which peptide is SEQ ID NO:14.

12. An immunogenic pharmaceutical composition comprising the immunogenic polypeptide of claim 8 and an immunologically and pharmaceutically acceptable vehicle or excipient.

13. An immunogenic pharmaceutical composition comprising the immunogenic polypeptide of claim 9 and an immunologically and pharmaceutically acceptable vehicle or excipient.

14. An immunogenic pharmaceutical composition comprising the immunogenic polypeptide of claim 10 and an immunologically and pharmaceutically acceptable vehicle or excipient.

15. An immunogenic pharmaceutical composition comprising the immunogenic polypeptide of claim 11 and an immunologically and pharmaceutically acceptable vehicle or excipient.

16. A kit comprising in separate compartments in close proximity therein:
(a) one or more unit doses of the immunogenic polypeptide of claim 8, and
(b) instructions for administering the immunogenic polypeptide or composition to a subject for inducing said broadly-neutralizing antibody response.

17. A kit comprising in separate compartments in close proximity therein:
(a) one or more unit doses of the immunogenic polypeptide of claim 9, and
(b) instructions for administering the immunogenic polypeptide or composition to a subject for inducing said broadly-neutralizing antibody response.

18. A kit comprising in separate compartments in close proximity therein:
(a) one or more unit doses of the immunogenic polypeptide of claim 10, and
(b) instructions for administering the immunogenic polypeptide or composition to a subject for inducing said broadly-neutralizing antibody response.

19. A kit comprising in separate compartments in close proximity therein:
(a) one or more unit doses of the immunogenic polypeptide of claim 11, and
(b) instructions for administering the immunogenic polypeptide or composition to a subject for inducing said broadly-neutralizing antibody response.

20. The immunogenic polypeptide of claim 1 wherein the length of the inserted cyclic V3 loop peptide or cyclic reverse V3 loop peptide is at least 18 amino acid residues.

21. The immunogenic polypeptide of claim 1 wherein the length of the inserted cyclic V3 loop peptide or cyclic reverse V3 loop peptide is at least 33 amino acid residues.

22. The immunogenic polypeptide of claim 1 wherein the length of the inserted cyclic V3 loop peptide or cyclic reverse V3 loop peptide is at least 35 amino acid residues.

23. A method for inducing a broadly neutralizing, cross-clade antibody response against a V3 epitope of HIV-1 gp120 in a subject in need thereof who has been primed against a V3 epitope, comprising administering to the subject an effective amount of the immunogenic polypeptide according to claim 8, wherein the response results in antibodies that neutralize HIV-1 viruses heterologous to the virus strain or clade from which the immunogenic polypeptide was derived.

24. A method for inducing a broadly neutralizing, cross-clade antibody response against a V3 epitope of HIV-1 gp120 in a subject in need thereof who has been primed against a V3 epitope, comprising administering to the subject an effective amount of the immunogenic pharmaceutical composition of claim 3.

25. A method for inducing a broadly neutralizing, cross-clade antibody response against a V3 epitope of HIV-1 gp120 in a subject in need thereof who has been primed against a V3 epitope, comprising administering to the subject an effective amount of the immunogenic pharmaceutical composition of claim 4.

26. A method for inducing a broadly neutralizing, cross-clade antibody response against a V3 epitope of HIV-1 gp120 in a subject in need thereof who has been primed against a V3 epitope, comprising administering to the subject an effective amount of the immunogenic polypeptide of claim 9.

27. A method for inducing a broadly neutralizing, cross-clade antibody response against a V3 epitope of HIV-1 gp120 in a subject in need thereof who has been primed against a V3 epitope, comprising administering to the subject an effective amount of the immunogenic polypeptide of claim 10.

28. A method for inducing a broadly neutralizing, cross-clade antibody response against a V3 epitope of HIV-1 gp120 in a subject in need thereof who has been primed against a V3 epitope, comprising administering to the subject an effective amount of the immunogenic polypeptide of claim 11.

29. A method for inducing a broadly neutralizing, cross-clade antibody response against a V3 epitope of HIV-1 gp120 in a subject in need thereof who has been primed against a V3 epitope, comprising administering to the subject an effective amount of the immunogenic pharmaceutical composition of claim 12.

30. A method for inducing a broadly neutralizing, cross-clade antibody response against a V3 epitope of HIV-1 gp120 in a subject in need thereof who has been primed against a V3 epitope, comprising administering to the subject an effective amount of the immunogenic pharmaceutical composition of claim 13.

31. A method for inducing a broadly neutralizing, cross-clade antibody response against a V3 epitope of HIV-1 gp120 in a subject in need thereof who has been primed against a V3 epitope, comprising administering to the subject an effective amount of the immunogenic pharmaceutical composition of claim 14.

32. A method for inducing a broadly neutralizing, cross-clade antibody response against a V3 epitope of HIV-1 gp120 in a subject in need thereof who has been primed against a V3 epitope, comprising administering to the subject an effective amount of the immunogenic pharmaceutical composition of claim 15.

33. A method for inducing a broadly neutralizing, cross-clade antibody response against a V3 epitope of HIV-1 gp120 in a subject in need thereof who has been primed against a V3 epitope, comprising administering to the subject an effective amount of the immunogenic polypeptide of claim 20.

34. A method for inducing a broadly neutralizing, cross-clade antibody response against a V3 epitope of HIV-1 gp120 in a subject in need thereof who has been primed against a V3 epitope, comprising administering to the subject an effective amount of the immunogenic polypeptide of claim 21.

35. A method for inducing a broadly neutralizing, cross-clade antibody response against a V3 epitope of HIV-1 gp120 in a subject in need thereof who has been primed against a V3 epitope, comprising administering to the subject an effective amount of the immunogenic polypeptide of claim 22.

* * * * *

```
                        SEQUENCE LISTING

<160> NUMBER OF SEQ ID NOS: 15

<210> SEQ ID NO 1
<211> LENGTH: 124
<212> TYPE: PRT
<213> ORGANISM: Vibrio cholerae
<220> FEATURE:
<223> OTHER INFORMATION: Cholera toxin B subunit

<400> SEQUENCE: 1

Met Ile Lys Leu Lys Phe Gly Val Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile His Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120

<210> SEQ ID NO 2
<211> LENGTH: 124
<212> TYPE: PRT
<213> ORGANISM: Escherichia coli
<220> FEATURE:
<223> OTHER INFORMATION: Heat-labile enterotoxin B subunit

<400> SEQUENCE: 2

Met Asn Lys Val Lys Cys Tyr Val Leu Phe Thr Ala Leu Leu Ser Ser
1               5                   10                  15

Leu Cys Ala Tyr Gly Ala Pro Gln Ser Ile Thr Glu Leu Cys Ser Glu
            20                  25                  30
```

Tyr Arg Asn Thr Gln Ile Tyr Thr Ile Asn Asp Lys Ile Leu Ser Tyr
            35                  40                  45

Thr Glu Ser Met Ala Gly Lys Arg Glu Met Val Ile Ile Thr Phe Lys
 50                  55                  60

Ser Gly Ala Thr Phe Gln Val Glu Val Pro Gly Ser Gln His Ile Asp
 65                  70                  75                  80

Ser Gln Lys Lys Ala Ile Glu Arg Met Lys Asp Thr Leu Arg Ile Thr
                 85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn
        115                 120

<210> SEQ ID NO 3
<211> LENGTH: 135
<212> TYPE: PRT
<213> ORGANISM: Artificial Sequence
<220> FEATURE:
<223> OTHER INFORMATION: synthetic

<400> SEQUENCE: 3

Thr Pro Gln Asn Ile Thr Asp Leu Cys Ala Glu Tyr His Asn Thr Gln
 1               5                  10                  15

Ile His Thr Leu Asn Asp Lys Ile Phe Ser Tyr Thr Glu Ser Leu Ala
             20                  25                  30

Gly Lys Arg Glu Met Ala Ile Ile Thr Phe Cys Thr Arg Pro Ser Asn
         35                  40                  45

Asn Thr Arg Lys Ser Ile His Ile Gly Pro Gly Arg Ala Phe Tyr Thr
 50                  55                  60

Thr Gly Glu Ile Ile Gly Asp Ile Arg Gln Ala His Cys Ala Thr Phe
 65                  70                  75                  80

Gln Val Glu Val Pro Gly Ser Gln His Ile Asp Ser Gln Lys Lys Ala
                 85                  90                  95

Ile Glu Arg Met Lys Asp Thr Leu Arg Ile Ala Tyr Leu Thr Glu Ala
            100                 105                 110

Lys Val Glu Lys Leu Cys Val Trp Asn Asn Lys Thr Pro Arg Ala Ile
        115                 120                 125

Ala Ala Ile Ser Met Ala Asn
    130                 135

<210> SEQ ID NO 4
<211> LENGTH: 35
<212> TYPE: PRT
<213> ORGANISM: Artificial Sequence
<220> FEATURE:
<223> OTHER INFORMATION: synthetic

<400> SEQUENCE: 4

Cys Thr Arg Pro Ser Asn Asn Thr Arg Lys Ser Ile His Ile Gly Pro
 1               5                  10                  15

Gly Arg Ala Phe Tyr Thr Thr Gly Glu Ile Ile Gly Asp Ile Arg Gln
             20                  25                  30

Ala His Cys
        35

<210> SEQ ID NO 5
<211> LENGTH: 113
<212> TYPE: PRT
<213> ORGANISM: Artificial Sequence

```
<220> FEATURE:
<223> OTHER INFORMATION: synthetic

<400> SEQUENCE: 5

Thr Pro Gln Asn Ile Thr Asp Leu Cys Ala Glu Tyr His Asn Thr Gln
1               5                   10                  15

Ile His Thr Leu Asn Asn Ser Ile Thr Ser Tyr Thr Glu Ser Leu Ala
            20                  25                  30

Gly Lys Arg Glu Met Ala Ile Ile Thr Phe Lys Arg Ile His Ile Gly
        35                  40                  45

Pro Gly Arg Ala Glu Tyr Gly Met Thr Phe Gln Val Glu Val Pro Gly
    50                  55                  60

Ser Gln His Ile Asp Ser Gln Lys Lys Ala Ile Glu Arg Met Lys Asp
65                  70                  75                  80

Thr Leu Arg Ile Ala Tyr Leu Thr Ser Ala Lys Val Glu Lys Leu Cys
                85                  90                  95

Val Trp Asn Asn Lys Thr Pro Arg Ala Ile Ala Ala Ile Ser Met Ala
                100                 105                 110

Asn

<210> SEQ ID NO 6
<211> LENGTH: 13
<212> TYPE: PRT
<213> ORGANISM: Artificial Sequence
<220> FEATURE:
<223> OTHER INFORMATION: synthetic

<400> SEQUENCE: 6

Lys Arg Ile His Ile Gly Pro Gly Arg Ala Glu Tyr Gly
1               5                   10

<210> SEQ ID NO 7
<211> LENGTH: 20
<212> TYPE: PRT
<213> ORGANISM: Artificial Sequence
<220> FEATURE:
<223> OTHER INFORMATION: synthetic

<400> SEQUENCE: 7

Ala Ile Ile Thr Phe Lys Arg Ile His Ile Gly Pro Gly Arg Ala Glu
1               5                   10                  15

Tyr Gly Met Thr
            20

<210> SEQ ID NO 8
<211> LENGTH: 19
<212> TYPE: PRT
<213> ORGANISM: Artificial Sequence
<220> FEATURE:
<223> OTHER INFORMATION: synthetic

<400> SEQUENCE: 8

Ala Cys Thr Arg Lys Ser Ile Arg Ile Gly Arg Gly Gln Thr Phe Tyr
1               5                   10                  15

Ala Cys Ala

<210> SEQ ID NO 9
<211> LENGTH: 13
<212> TYPE: PRT
<213> ORGANISM: Artificial Sequence
<220> FEATURE:
<223> OTHER INFORMATION: synthetic
```

```
<220> FEATURE:
<221> NAME/KEY: misc_feature
<222> LOCATION: (1)..(1)
<223> OTHER INFORMATION: Residue 1 is modified by a NH2 group.
<220> FEATURE:
<221> NAME/KEY: misc_feature
<222> LOCATION: (9)..(9)
<223> OTHER INFORMATION: Residue 9 is modified by a COOH group.

<400> SEQUENCE: 9

Arg Lys Ser Ile His Ile Gly Pro Gly Gln Ala Phe Tyr
1               5                   10

<210> SEQ ID NO 10
<211> LENGTH: 18
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Residue 1 is modified by a NH2 group.
<220> FEATURE:
<221> NAME/KEY: misc_feature
<222> LOCATION: (9)..(9)
<223> OTHER INFORMATION: Residue 9 is modified by a COOH group.

<400> SEQUENCE: 10

Cys Gln Ala Phe Tyr Ala Ser Ser Pro Arg Lys Ser Ile His Ile Gly
1               5                   10                  15

Ala Cys

<210> SEQ ID NO 11
<211> LENGTH: 4
<212> TYPE: PRT
<213> ORGANISM: Artificial Sequence
<220> FEATURE:
<223> OTHER INFORMATION: synthetic

<400> SEQUENCE: 11

Gly Pro Gly Gln
1

<210> SEQ ID NO 12
<211> LENGTH: 4
<212> TYPE: PRT
<213> ORGANISM: Artificial Sequence
<220> FEATURE:
<223> OTHER INFORMATION: synthetic

<400> SEQUENCE: 12

Gly Pro Gly Arg
1

<210> SEQ ID NO 13
<211> LENGTH: 29
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Residue 1 is modified by a NH2 group.
<220> FEATURE:
<221> NAME/KEY: misc_feature
<222> LOCATION: (9)..(9)
<223> OTHER INFORMATION: Residue 9 is modified by a COOH group.
```

```
<400> SEQUENCE: 13

Asn Asn Thr Arg Lys Ser Ile His Ile Gly Pro Gly Gln Ala Phe Tyr
1               5                   10                  15

Ala Thr Gly Asp Ile Ile Gly Asp Ile Arg Gln Ala His
            20                  25

<210> SEQ ID NO 14
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Residue 1 is modified by a NH2 group.
<220> FEATURE:
<221> NAME/KEY: misc_feature
<222> LOCATION: (9)..(9)
<223> OTHER INFORMATION: Residue 9 is modified by a COOH group.

<400> SEQUENCE: 14

Cys Gln Ala Phe Tyr Ala Thr Gly Asp Ile Ile Gly Asp Ile Arg Gln
1               5                   10                  15

Ala His Ser Gly Pro Asn Asn Thr Arg Lys Ser Ile His Ile Gly Ala
            20                  25                  30

Cys

<210> SEQ ID NO 15
<211> LENGTH: 118
<212> TYPE: PRT
<213> ORGANISM: Artificial Sequence
<220> FEATURE:
<223> OTHER INFORMATION: synthetic

<400> SEQUENCE: 15

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Cys Gln Ala Phe Tyr Ala
        35                  40                  45

Ser Ser Pro Arg Lys Ser Ile His Ile Gly Ala Cys Ala Thr Phe Gln
    50                  55                  60

Val Glu Val Pro Gly Ser Gln His Ile Asp Ser Gln Lys Lys Ala Ile
65                  70                  75                  80

Glu Arg Met Lys Asp Thr Leu Arg Ile Ala Tyr Leu Thr Glu Ala Lys
                85                  90                  95

Val Glu Lys Leu Cys Val Trp Asn Asn Lys Thr Pro Arg Ala Ile Ala
            100                 105                 110

Ala Ile Ser Met Ala Asn
            115
```